United States Patent
LaVon et al.

(10) Patent No.: US 6,989,005 B1
(45) Date of Patent: Jan. 24, 2006

(54) ABSORBENT ARTICLES HAVING REMOVABLE COMPONENTS

(75) Inventors: Gary Dean LaVon, Middletown, OH (US); Gerald Alfred Young, Cincinnati, OH (US); Theodora Beck, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/828,005

(22) Filed: Mar. 27, 1997

(51) Int. Cl.
*A61F 13/15* (2006.01)
*A61F 13/20* (2006.01)

(52) U.S. Cl. ................. 604/385.14; 604/368; 604/369; 604/370; 604/374; 604/377; 604/378; 604/394; 604/395; 604/398

(58) Field of Classification Search ................ 604/386, 604/391, 393–402, 368, 369, 370, 372, 374, 604/378, 385.01, 385.14, 385.15, 385.19; 602/67–73; 2/400–409
See application file for complete search history.

(56) References Cited

U.S. PATENT DOCUMENTS

| | | | | |
|---|---|---|---|---|
| 833,849 A | * | 10/1906 | Schiff | 604/396 |
| 1,695,109 A | * | 12/1928 | Kosloff | 604/397 |
| 1,893,745 A | * | 1/1933 | Josias | 604/398 |
| 2,468,445 A | * | 4/1949 | Hurst | 604/397 |
| 2,476,585 A | * | 7/1949 | Cohan | 2/408 |
| 2,530,647 A | * | 11/1950 | Bucher | 604/395 |
| 2,574,279 A | * | 11/1951 | Oberle | 604/397 |
| 2,688,328 A | * | 9/1954 | Marcus | 604/397 |
| 2,695,025 A | * | 11/1954 | Andrews | 604/398 |
| 2,826,199 A | * | 3/1958 | Brandon | 604/397 |
| 2,832,346 A | * | 4/1958 | Morstad | 604/398 |
| 2,842,129 A | * | 7/1958 | Ernstorff | 604/398 |
| 2,868,205 A | * | 1/1959 | Epstein | 604/399 |
| 3,050,063 A | | 8/1962 | Margraf | |
| 3,162,196 A | | 12/1964 | Salk | |
| 3,306,293 A | * | 2/1967 | Marder et al. | 604/392 |
| 3,595,235 A | | 7/1971 | Jespersen | |
| 3,658,064 A | | 4/1972 | Pociluyko | |
| 3,771,524 A | | 11/1973 | Ralph | |
| 3,848,594 A | | 11/1974 | Buell | |
| 3,860,003 A | | 1/1975 | Buell | |
| 3,886,941 A | | 6/1975 | Duane et al. | |
| 3,926,189 A | * | 12/1975 | Taylor | 604/369 |
| 4,019,517 A | | 4/1977 | Glassman | |
| 4,022,210 A | | 5/1977 | Glassman | |
| 4,072,150 A | | 2/1978 | Glassman | |
| 4,081,301 A | | 3/1978 | Buell | |
| 4,257,418 A | | 3/1981 | Hessner | |
| 4,260,443 A | | 4/1981 | Lindsay et al. | |

(Continued)

FOREIGN PATENT DOCUMENTS

CN 2073744 U 3/1991

(Continued)

*Primary Examiner*—Karin Reichle
(74) *Attorney, Agent, or Firm*—Michael P. Hayden; Roddy M. Bullock; Ken K. Patel

(57) ABSTRACT

A disposable absorbent article suitable for absorbing and retaining aqueous body fluids includes a backsheet that is substantially liquid impervious except at a discontinuity therein and an absorbent core between the backsheet and a topsheet. The absorbent core includes a non-removable component and a removable and replaceable component in fluid communication with the non-removable component. Access for the removal and replacement of the removable component is provided by the discontinuity in the backsheet. The replaceable absorbent core component may be removed and a like component may be substituted in place of the removed component without removal of the absorbent article from the wearer.

19 Claims, 12 Drawing Sheets

U.S. PATENT DOCUMENTS

| | | | |
|---|---|---|---|
| 4,265,245 A | 5/1981 | Glassman | |
| 4,326,302 A | 4/1982 | Lowe et al. | |
| 4,467,012 A | 8/1984 | Pedersen et al. | |
| 4,496,360 A | 1/1985 | Joffe et al. | 604/397 |
| 4,515,595 A | 5/1985 | Kievit et al. | |
| 4,560,381 A | 12/1985 | Southwell | |
| 4,578,073 A | 3/1986 | Dysart et al. | 604/397 |
| 4,597,760 A | 7/1986 | Buell | 604/397 |
| 4,597,761 A | 7/1986 | Buell | 604/397 |
| 4,615,695 A * | 10/1986 | Cooper | 604/385.15 |
| 4,625,001 A | 11/1986 | Tsubakimoto et al. | |
| 4,654,039 A | 3/1987 | Brandt et al. | |
| 4,666,983 A | 5/1987 | Tsubakimoto et al. | |
| 4,695,278 A | 9/1987 | Lawson | |
| 4,710,188 A | 12/1987 | Runeman | |
| 4,715,918 A | 12/1987 | Lang | |
| 4,770,656 A | 9/1988 | Proxmire et al. | 604/393 |
| 4,773,903 A | 9/1988 | Weisman et al. | |
| D298,566 S | 11/1988 | Runeman | |
| 4,808,178 A | 2/1989 | Aziz et al. | |
| 4,816,025 A | 3/1989 | Foreman | |
| 4,834,736 A | 5/1989 | Boland et al. | 604/385.2 |
| 4,834,737 A | 5/1989 | Khan | |
| 4,834,738 A | 5/1989 | Kielpikowski et al. | 604/385.2 |
| 4,851,069 A | 7/1989 | Packard et al. | |
| 4,872,871 A | 10/1989 | Proxmire et al. | 604/394 |
| 4,892,598 A | 1/1990 | Stevens et al. | 156/91 |
| 4,923,454 A | 5/1990 | Seymour et al. | |
| 4,938,756 A | 7/1990 | Salek | |
| 4,950,264 A | 8/1990 | Osborn, III | |
| 4,964,860 A | 10/1990 | Gipson et al. | 604/391 |
| 4,968,312 A | 11/1990 | Khan | |
| 4,988,344 A | 1/1991 | Reising et al. | |
| 4,988,345 A | 1/1991 | Reising | |
| 4,994,037 A | 2/1991 | Bernardin | |
| 5,009,650 A | 4/1991 | Bernardin | |
| 5,009,653 A | 4/1991 | Osborn, III | |
| 5,061,259 A | 10/1991 | Goldman et al. | |
| 5,102,597 A | 4/1992 | Roe et al. | |
| 5,128,082 A | 7/1992 | Makoui | |
| 5,147,345 A | 9/1992 | Young et al. | |
| 5,149,335 A | 9/1992 | Kellenberger et al. | |
| 5,167,655 A * | 12/1992 | McCoy | 604/395 |
| 5,176,668 A | 1/1993 | Bernardin | |
| 5,188,624 A | 2/1993 | Young, Sr. et al. | 604/378 |
| 5,207,662 A | 5/1993 | James | |
| 5,207,663 A * | 5/1993 | McQueen | 604/396 |
| 5,217,445 A | 6/1993 | Young et al. | |
| 5,260,345 A | 11/1993 | DesMarais et al. | |
| 5,268,224 A | 12/1993 | DesMarais et al. | |
| 5,318,554 A * | 6/1994 | Young et al. | 604/378 |
| 5,324,561 A | 6/1994 | Rezai et al. | |
| 5,325,543 A * | 7/1994 | Allen | 2/406 |
| 5,358,500 A | 10/1994 | LaVon et al. | |
| 5,383,867 A * | 1/1995 | Klinger | 604/398 |
| 5,387,207 A * | 2/1995 | Dyer et al. | 604/369 |
| 5,401,266 A | 3/1995 | Runeman et al. | |
| 5,405,342 A | 4/1995 | Roessler et al. | 604/364 |
| 5,409,476 A | 4/1995 | Coates | 604/391 |
| 5,458,591 A | 10/1995 | Roessler et al. | 604/364 |
| 5,476,457 A | 12/1995 | Roessler et al. | 604/364 |
| 5,486,168 A | 1/1996 | Runeman et al. | |
| 5,531,728 A | 7/1996 | Lash | |
| 5,549,589 A | 8/1996 | Horney et al. | |
| 5,550,167 A * | 8/1996 | DesMarais | 604/369 |
| 5,556,393 A | 9/1996 | Rönnberg | |
| 5,563,179 A * | 10/1996 | Stone et al. | |
| 5,569,229 A * | 10/1996 | Rogers | 604/395 |
| 5,613,959 A | 3/1997 | Roessler et al. | |
| 5,636,387 A * | 6/1997 | Lundy | 604/395 |
| 5,650,222 A | 7/1997 | DesMarais et al. | 604/369 |
| 5,800,416 A | 9/1998 | Seger et al. | |
| 5,817,081 A * | 10/1998 | LaVon et al. | |
| 5,827,253 A * | 10/1998 | Young et al. | 604/369 |
| 5,843,055 A | 12/1998 | Seger | |
| 5,843,065 A * | 12/1998 | Wyant | 604/398 |
| 5,906,602 A * | 5/1999 | Weber et al. | |
| 6,015,935 A * | 1/2000 | LaVon et al. | 604/378 |
| 6,083,210 A * | 7/2000 | Young et al. | 604/367 |
| 6,229,061 B1 * | 5/2001 | Dragoo et al. | 604/358 |
| 2002/0091368 A1 * | 7/2002 | LaVon et al. | 604/385.14 |
| 2003/0199844 A1 * | 10/2003 | LaVon et al. | 604/385.14 |
| 2003/0220623 A1 | 11/2003 | Sugiyama et al. | |
| 2004/0024379 A1 | 2/2004 | LaVon et al. | |
| 2004/0030314 A1 | 2/2004 | LaVon et al. | |
| 2004/0039361 A1 | 2/2004 | LaVon et al. | |

FOREIGN PATENT DOCUMENTS

| | | | |
|---|---|---|---|
| EP | 0 319 314 A2 | 6/1989 | |
| EP | 0 584 757 A1 | 3/1994 | |
| EP | 0 585 766 A1 | 3/1994 | |
| GB | 0493819 * | 10/1938 | 604/386 |
| GB | 0734994 * | 8/1958 | 604/398 |
| GB | 1411087 * | 10/1975 | 2/406 |
| GB | 2 042 342 | 9/1980 | |
| GB | 2 295 321 | 5/1996 | |
| JP | 6121812 * | 5/1997 | 604/387 |
| WO | WO 91/10413 | 7/1991 | |
| WO | 91110871 * | 11/1991 | |
| WO | 95/17870 | 7/1995 | |

* cited by examiner

ABSORBENT ARTICLES HAVING REMOVABLE COMPONENTS

FIELD OF THE INVENTION

This invention relates to absorbent articles, such as disposable diapers. This invention further relates to absorbent articles having multi-piece absorbent cores.

BACKGROUND OF THE INVENTION

Absorbent articles such as disposable diapers, incontinence pads, training pants, and catamenial napkins generally include an absorbent core for receiving and holding body exudates. The absorbent core typically includes a fibrous web, which can be a nonwoven, airlaid web of natural or synthetic fibers, or combinations thereof. Fibrous webs used in such absorbent articles also often include certain absorbent gelling materials usually referred to as "hydrogels," "superabsorbent" or "hydrocolloid" materials to store large quantities of the discharged body fluids. These materials absorb through capillary or osmotic forces, or a combination of both.

An alternative absorbent material capable of providing capillary fluid transport is open-celled polymeric foams. If made appropriately, open-celled polymeric foams provide features of capillary fluid acquisition, transport, and storage required for use in high performance absorbent cores for absorbent articles such as diapers. Absorbent articles containing such foams may also possess desirable wet integrity, provide suitable fit throughout the entire period the article is worn, and may avoid changes in shape during use. In addition, absorbent articles containing such absorbent foam structures could be easier to manufacture on a commercial scale. For example, absorbent foam diaper cores could simply be stamped out of continuous foam sheets and could be designed to have considerably greater integrity and uniformity than air-laid fibrous absorbent cores containing particulate absorbent gelling materials.

Besides absorbency and manufacturing ease, another desirable property of open-celled polymeric foams is the ability to make shaped or contoured absorbent cores having various shape configurations, fluid absorbency properties, and wear characteristics. Shaped or contoured absorbent cores made from foam materials have been disclosed in the diaper art. Shaped or contoured absorbent cores made from open-celled foam materials having particularly desirable fluid transport characteristics are disclosed in U.S. Pat. No. 5,147,345 ('345 patent) issued to Young et al. on Sep. 15, 1992 and hereby incorporated herein by reference. The Young et al. '345 core essentially comprises both a fluid acquisition/distribution component and a fluid storage/redistribution component. The fluid acquisition/distribution component is positioned within the absorbent article in such a way as to receive or contact aqueous body fluid which has been discharged into the absorbent article by the wearer of the article. The fluid storage/redistribution component in turn is positioned within the article to be in fluid communication with the fluid acquisition/distribution component.

Multipiece cores providing for the absorbent characteristics of the Young et al. '345 patent in a preferred configuration are disclosed in U.S. Pat. No. 5,906,602 to Weber et al. Weber et al. discloses shaped absorbent cores comprising a front panel and a back panel. The front and back panels are in fluid communication with a center section. Preferably the center section comprises material generally suitable for fluid acquisition/distribution, while the front and back panels comprise material generally suitable for fluid storage/redistribution.

Despite the advances in absorbent articles and in fluid handling absorbent core materials, absorbent articles having multiple absorbent core components, as well as unitary cores, are generally designed for single use wear. Once the storage/redistribution component is saturated with bodily discharges, such as urine, the entire absorbent article is generally discarded and replaced. Often parts of the absorbent article are still usable, and except for being unitary with the absorbent cores, these parts could be used further. In addition to the added cost and waste associated with discarding reusable materials, it is often inconvenient to remove and replace the entire absorbent article when absorbent core components are saturated.

Absorbent articles with removable absorbent inserts are known in the art. For example, U.S. Pat. No. 4,597,761 to Buell, issued Jul. 1, 1986, discloses a disposable absorbent insert for use inside an over-garment such as a conventional reusable diaper, or a disposable diaper. Once the absorbent insert becomes saturated it may be removed and discarded. The absorbent article may then be reused with a fresh absorbent insert. Buell is representative of a general absorbent article design having a continuous fluid impervious backing sheet (backsheet) and a fluid pervious bodyside liner (topsheet) with a removable absorbent core insert disposed between. The absorbent core insert is removed from the body side of the article, necessarily requiring that the absorbent article be removed from the wearer. This removal is often inconvenient and time consuming.

Accordingly, it would be desirable to have an absorbent article that has removable or replaceable absorbent core components wherein the absorbent core components can be removed or replaced without having to remove the absorbent article from the wearer.

Additionally, it would be desirable to have an absorbent article that has an absorbent core having removable or replaceable components and a discontinuous backsheet, allowing saturated portions of the absorbent core to be removed through the backsheet discontinuity, thereby exposing unsaturated portions and allowing for prolonged use of portions of an absorbent article.

Further, it would be desirable to have an absorbent article with a continuous backsheet affixed to a topsheet about a periphery that has removable or replaceable absorbent core components disposed between the topsheet and backsheet, such that access to absorbent core components is provided by separating the topsheet and backsheet in a predetermined area to form an opening.

SUMMARY OF THE INVENTION

The present invention relates to disposable absorbent articles suitable for absorbing and retaining aqueous body fluids. The absorbent article comprises at least one removable absorbent core component, a first waist region, a second waist region, and a crotch region positioned between the first waist region and the second waist region. The absorbent article further comprises: (a) a backsheet joined to a fluid pervious topsheet, the backsheet comprising a web and being substantially liquid impervious except at at least one discontinuity in the web; and (b) an absorbent core disposed between the topsheet and the backsheet, the absorbent core comprising a non-removable absorbent core component disposed in at least the crotch region and at least one removable absorbent core component removably disposed in the first waist region and in fluid communication with the non-removable absorbent core component; wherein the backsheet further comprises access means for providing access to the removable absorbent core component through the backsheet so that the removable absorbent core component may be removed from the absorbent article through the backsheet without having to remove the absorbent article from a wearer, the access means comprising the discontinuity and being positioned in the first waist region, a recloseable flap secured over the discontinuity, and a fastener for recloseably joining the flap to the backsheet.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

Figure 1:
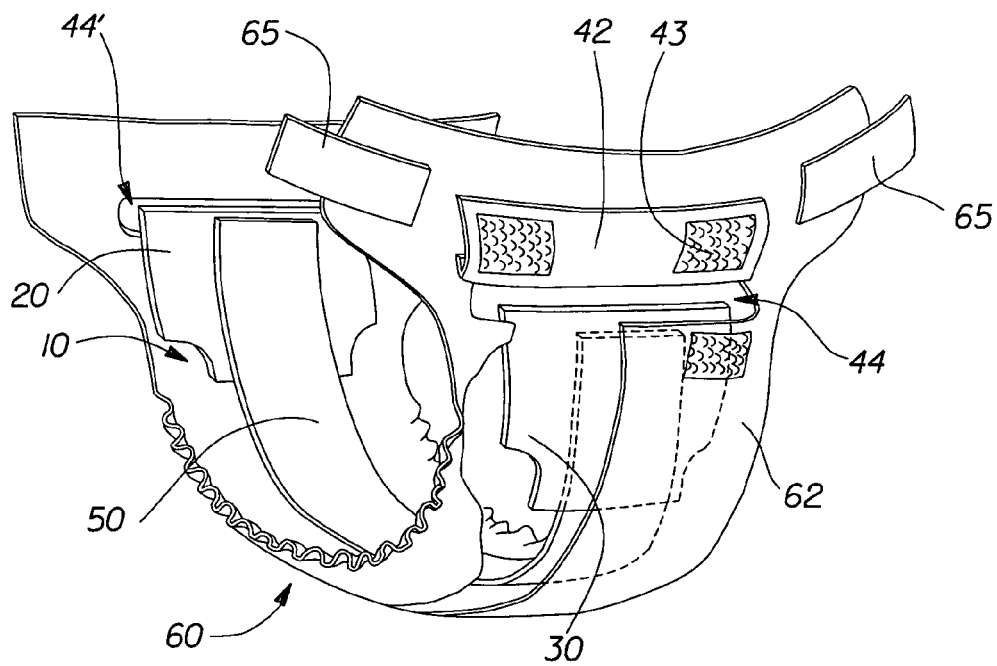
FIG. 1 is a perspective, partially segmented illustration of an embodiment of an absorbent article according to the present invention.

As used herein, the term "absorbent core" refers to a material or combination of materials suitable for absorbing, distributing, and storing aqueous fluids such as body exudates. As used herein, the term "absorbent core component" refers to one of a plurality of absorbent core pieces in a multi-piece absorbent core. As used herein, the term "absorbent core member" refers to one of a plurality of pieces of an absorbent core component, preferably pieces in a layered relationship. The term "absorbent article" refers to devices which absorb and contain body exudates by use of an absorbent core, and, more specifically, refers to devices which are placed against or in proximity to the body of the wearer to absorb and contain the various exudates discharged from the body. A referred embodiment of an absorbent article of the present invention is the disposable absorbent article, diaper 60, as shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, training pants, pull-on diapers, and the like.

The term "disposable" is used herein to describe absorbent articles which are not intended to be laundered or otherwise restored or reused as an absorbent article, i.e., that are intended to be discarded after a single use and, preferably, to be recycled, composted or otherwise disposed of in an environmentally compatible manner. Note that, as described in this disclosure, a single use of a chasis, e.g. topsheet backsheet, fasteners, and a non-removable absorbent core component may correspond to several removals of removable core components or replacements of replaceable absorbent core components. However, each element is intended to be discarded after having been once wetted by bodily fluids and removed from the wearer's body, rather than being restored and reapplied to the wearer's body.

FIG. 1 shows in perspective a partially segmented illustration of an embodiment of an absorbent article 60 according to the present invention. The multipiece absorbent core 10 comprising multiple absorbent core components, such as center section 50, front panel 20, and back panel 30, is more fully illustrated and described below with reference to FIG. 9. The multipiece absorbent core 10 is also fully disclosed in U.S. Pat. No. 5,906,602 to Weber et al., which is hereby incorporated herein by reference.

By forming the absorbent core having discrete components, several desirable results are obtained. First, the core exhibits desirable aesthetics and fit when used in an absorbent article of the present invention due to the use of discontinuous strips or panels of absorbent material. For example, the center section may comprise separate strips or layers, allowing the center section to bend and buckle somewhat independently from adjacent strips (and the front and rear panels) to provide better fit and comfort in the crotch area than is achieved with one-piece absorbent cores.

A second advantage to having the core formed in sections is the ability to independently vary many of the characteristics of the absorbent members. These variations include the acquisition rates, distribution rates, storage capacities and rates, thickness, functionality, and the shape or configuration of the absorbent strips or panels. For example, in a preferred embodiment of an absorbent article of the present invention, three absorbent strip members comprise the center section, with one of the absorbent strip members having relatively greater acquisition characteristics, and the remaining two having relatively greater storage/distribution characteristics.

Figure 2:
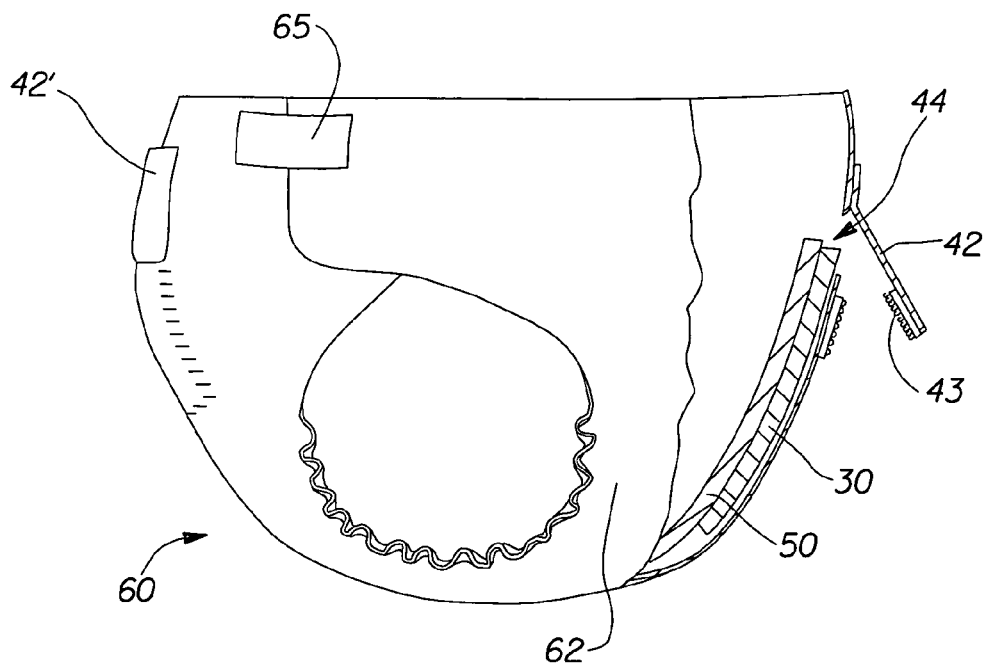
FIG. 2 is a side view, showing in partial cross-section, the absorbent article of FIG. 1.

A third benefit resulting from the multipiece absorbent core when used in an absorbent article of the present invention is the capability of removing and/or replacing core components of the absorbent core to regenerate the storage/redistribution capacity of the absorbent core 10. As shown in FIG. 1, a discontinuity in backsheet 62 forms aperture 44 and provides access to the absorbent core components, for example, back panel 30; therefore allowing for removal or replacement of absorbent core components. FIG. 2 shows in partial cross-section the absorbent article embodiment shown in perspective in FIG. 1. Additional description of a representative disposable diaper in accordance with the present invention is disclosed below with reference to FIG. 9.

As shown in FIGS. 1 and 2, when disposable diaper 60 is being worn, flap 42 may be secured over aperture 44 by suitable fasteners 43, such as VELCRO strips or adhesive strips (not shown). More preferably, flap 42 is sealed with releasable adhesive, thereby providing for fluid impermeability when closed, but allowing for multiple openings and closings. Aperture 44 forms what may be described as a pocket or pouch, with absorbent core components, for example, back panel 30 being removable and replaceable through the aperture 44. As shown in FIGS. 1 and 2, to remove back panel 30, flap 42 is lifted to form opening 41, and back panel 30 is extracted out of the absorbent article through aperture 44. To replace back panel 30, a fresh, dry absorbent component may be reinserted through backsheet 62 through aperture 44. FIG. 2 shows flap 42' in the closed position over aperture 44' corresponding to front panel 20 (shown in FIG. 1). In general, back panel 30, front panel 20, and corresponding apertures 44 and 44' and flaps 42 and 42' are substantially similar, but need not be. In an alternative embodiment, it may only be desired to include one aperture 44 and flap 42, for example, for access to back panel 30.

By replacing absorbent components, particularly absorbent components that are primarily suited for storage/redistribution, the use of the absorbent article, such as disposable diaper 60, may be prolonged while continuing to draw moisture away from the wearer's skin. As storage/redistribution absorbent core components, e.g., front panel 20 and back panel 30, become saturated, they may become substantially less effective at absorbing moisture from acquisition/distribution components of center section 50. Consequently, center section 50 becomes more saturated, thereby hindering its ability to absorb as much moisture away from the wearer's skin. However, once absorbent core components such as back panel 30 are replaced, the absorbent suction of the core is regenerated, and once again becomes capable of absorbing moisture from the acquisition/distribution components of center section 50. Therefore, the disposable diaper may be worn longer, and regeneration of the absorbent core may be made without removal of the diaper from the wearer.

Figure 3:
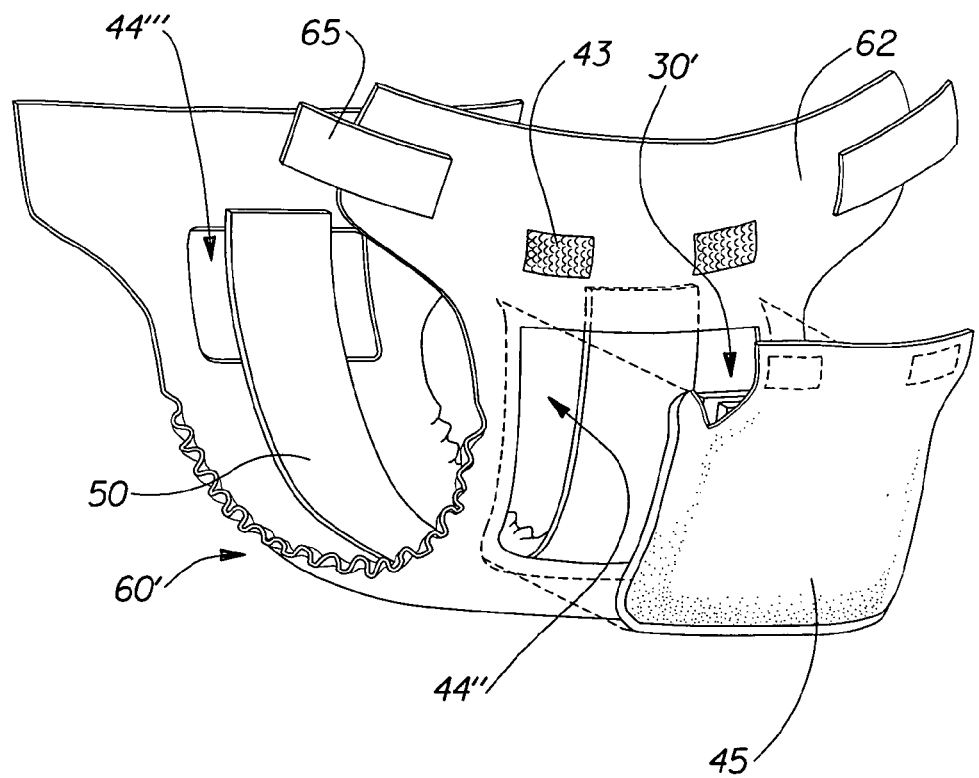
FIG. 3 is an exploded, perspective, partially segmented illustration of a preferred embodiment of an absorbent article according to the present invention.
Figure 4:
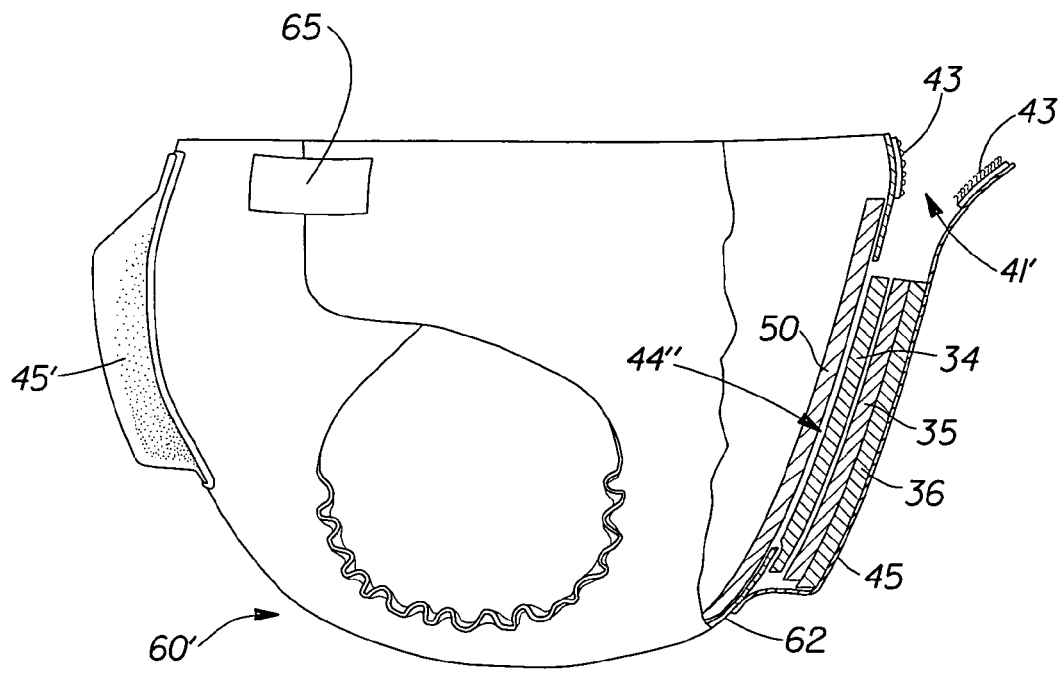
FIG. 4 is a side view, showing in partial cross-section, a preferred embodiment of the absorbent article of FIG. 3.

In a preferred embodiment of the absorbent article 60 of the present invention, a discontinuity in backsheet 62 forms an aperture, e.g., aperture 44", in the general proximity of and rear panel 30' and/or aperture 44''' in the proximity of a front panel (not shown), as shown in FIGS. 3 and 4. In this preferred embodiment a backsheet pocket 45 may be affixed adjacent aperture 44". Backsheet pocket 45 and backsheet pocket 45' serve to contain and position back panel 30' and a front panel (not shown) as components made up of layered members, e.g., individual back panel members 34, 35, and 36 in FIG. 4. As one back panel member, e.g., back panel member 34, becomes saturated with bodily discharge it may be removed through opening 41', exposing a fresh, dry back panel member, e.g., back panel member 35. Backsheet pocket 45 is preferably resilient and pliable, and is a substantially fluid impervious barrier over aperture 44", functionally becoming an extension of backsheet 62.

Backsheet pocket 45 is reclosable and preferably resealable, and is preferably positioned so that as it is secured in a closed position a back panel member, e.g., back panel member 35, is urged into fluid communication with center section 50.

Figure 5:
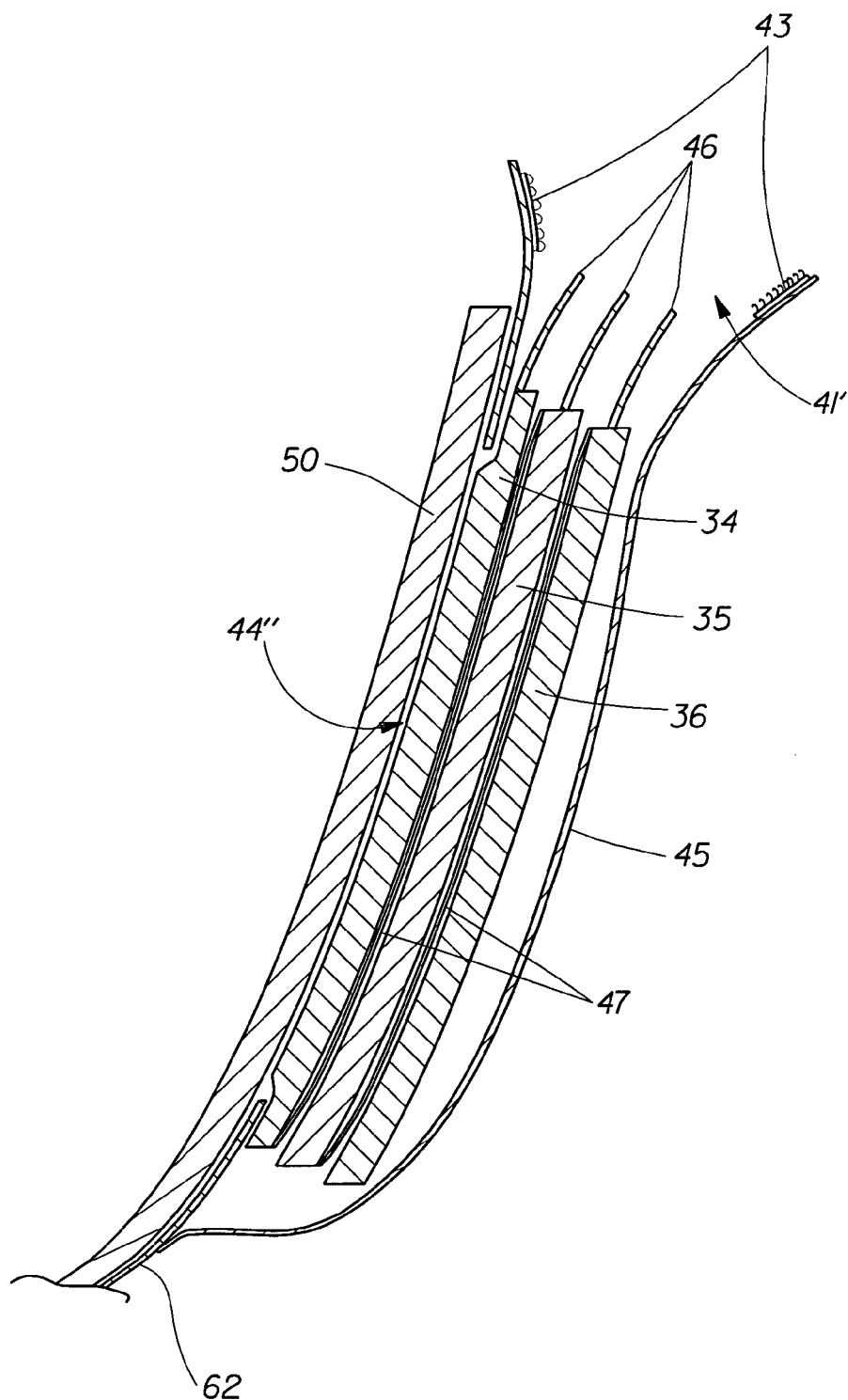
FIG. 5 is a cross-section illustration of a preferred embodiment of a backsheet opening configuration in an absorbent article according to the present invention.

FIG. 5 shows a preferred embodiment of the arrangement of back panel 30', again showing representative pack panel members 34, 35, and 36 in a layered relationship adjacent aperture 44" and in fluid communication with center section 50. It is understood that the description in terms of back panels is equally applicable to front panels. Removal of back panel members through opening 41' may be facilitated by the use of pull tabs, e.g., tabs 46, which may be of any type known in the art, such as a strip of plastic film adhered to each back panel member. Additionally, back panel members may be separated from one another by a fluid impervious blocking layer 47 so that adjacent back panel members are not in fluid communication with each other. Blocking layer 47 may be any fluid impervious polymer film, such as film suitable for use as a fluid impervious backsheet. As one back panel member becomes saturated by absorption of fluid from center section 50, it may be removed, thereby exposing a substantially dry, fresh back panel member for additional absorption from center section 50. In this manner, the absorbent article may be refreshed or regenerated for a prolonged period of time without removal from the wearer.

Figure 6:
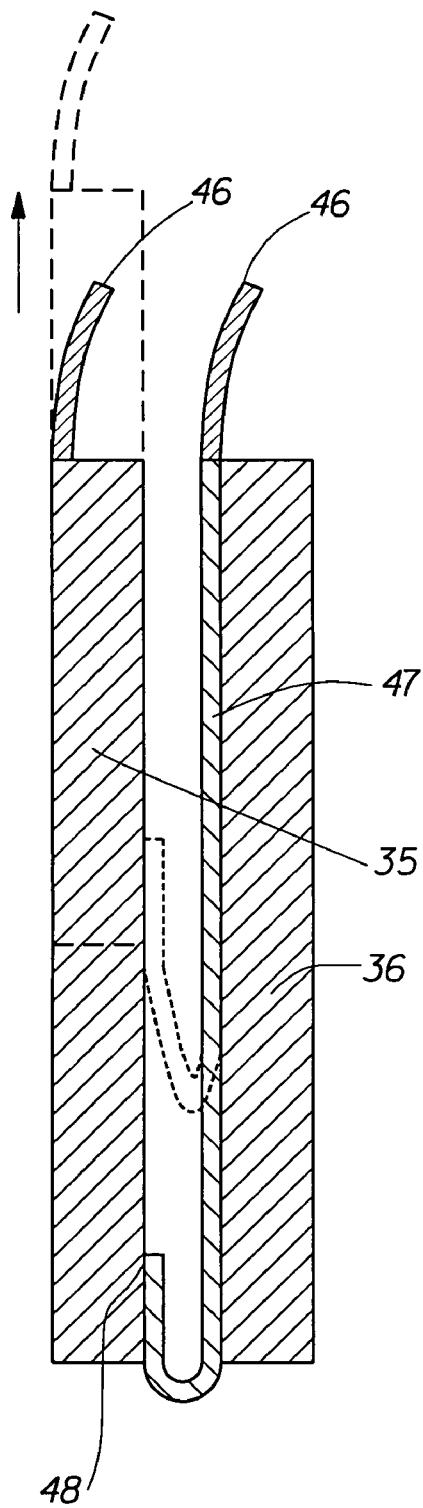
FIG. 6 is a cross-section detail of a preferred configuration of removable absorbent core components.

FIG. 6 shows a particularly preferred embodiment of the arrangement of back panel members. It is understood that the disclosure in terms of back panel members is equally applicable to front panel members. Back panel members 35 and 36 are shown as representative of back panel component 30' in a layered relationship with fluid impervious blocking layer 47 disposed between them. Blocking layer 47 is in a layered relationship with back panel members 35 and 36 and forms a fluid impervious layer between them. A portion of blocking layer 47 is preferably affixed, for example at attachment point 48, to the back panel member being removed. As a substantially saturated back panel member, e.g. back panel member 35, is removed, blocking layer 47 is removed as well, thereby leaving the adjacent back panel member, e.g., back panel member 36, in position to be urged into fluid communication with center section 50.

Figure 7:
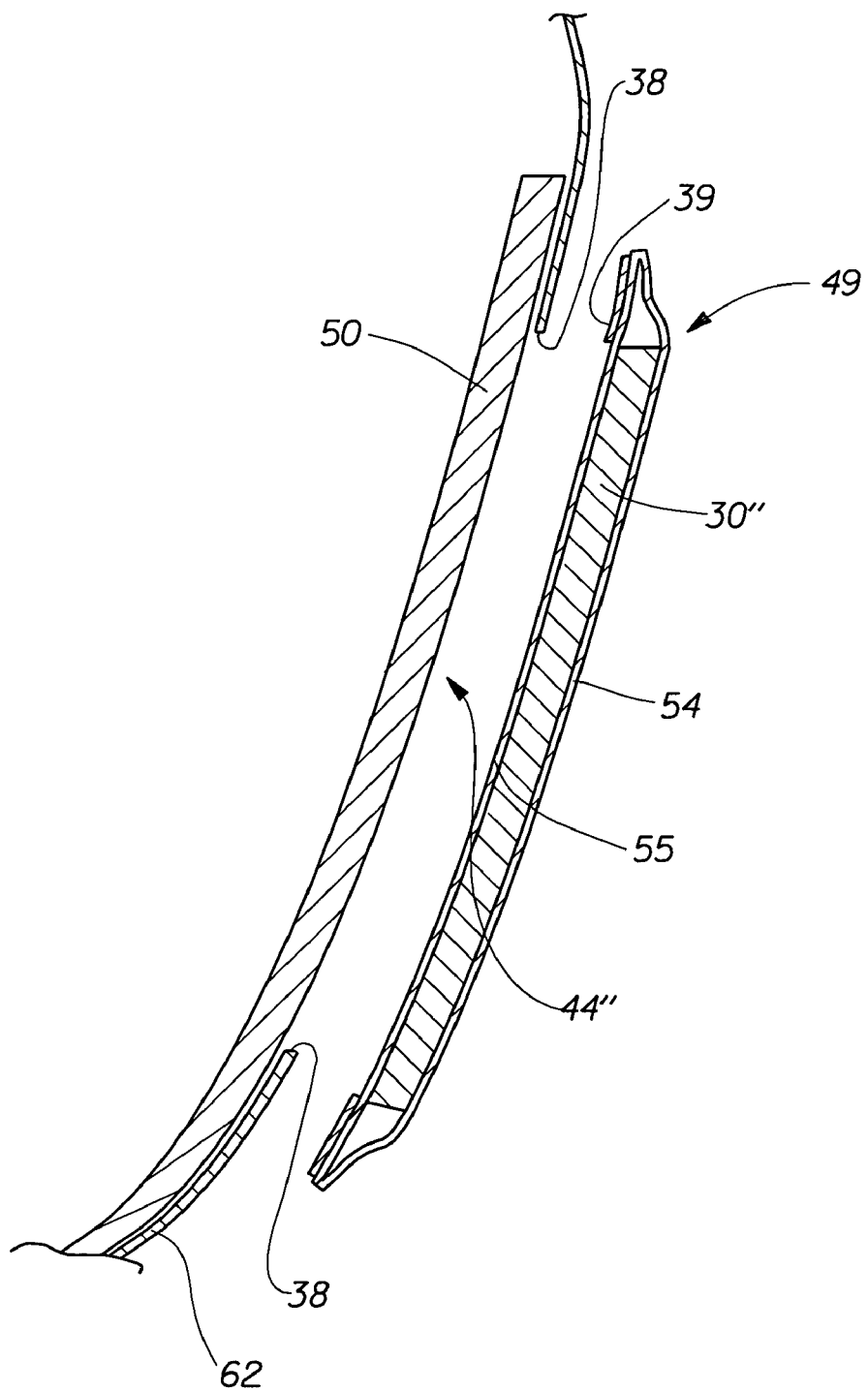
FIG. 7 is a cross-section depicting an alternative method of providing for a removable and replaceable absorbent core component of an absorbent article according to the present invention.

An alternative embodiment of the front and back panels of an absorbent article of the present invention is shown in cross-section in FIG. 7. While illustrated in terms of back panel, it is understood that the description is equally applicable to front panels. As shown in FIG. 7, rather than providing a backsheet pocket 45 affixed to backsheet 62, a back panel envelope 49 is provided. Back panel envelope 49 has a single back panel 30" enveloped between a substantially fluid impervious layer 54 and a substantially fluid pervious layer 55, and may be affixed, for example, by suitable adhesives 39 known in the art, to the backsheet 62 adjacent to the perimeter 38 of aperture 44". Preferably back panel envelope 49 is removably affixed so that as back panel 30" becomes saturated due to absorption of fluid from center section 50 it may be removed and replaced with a fresh, dry back panel envelope 49.

Figure 8:
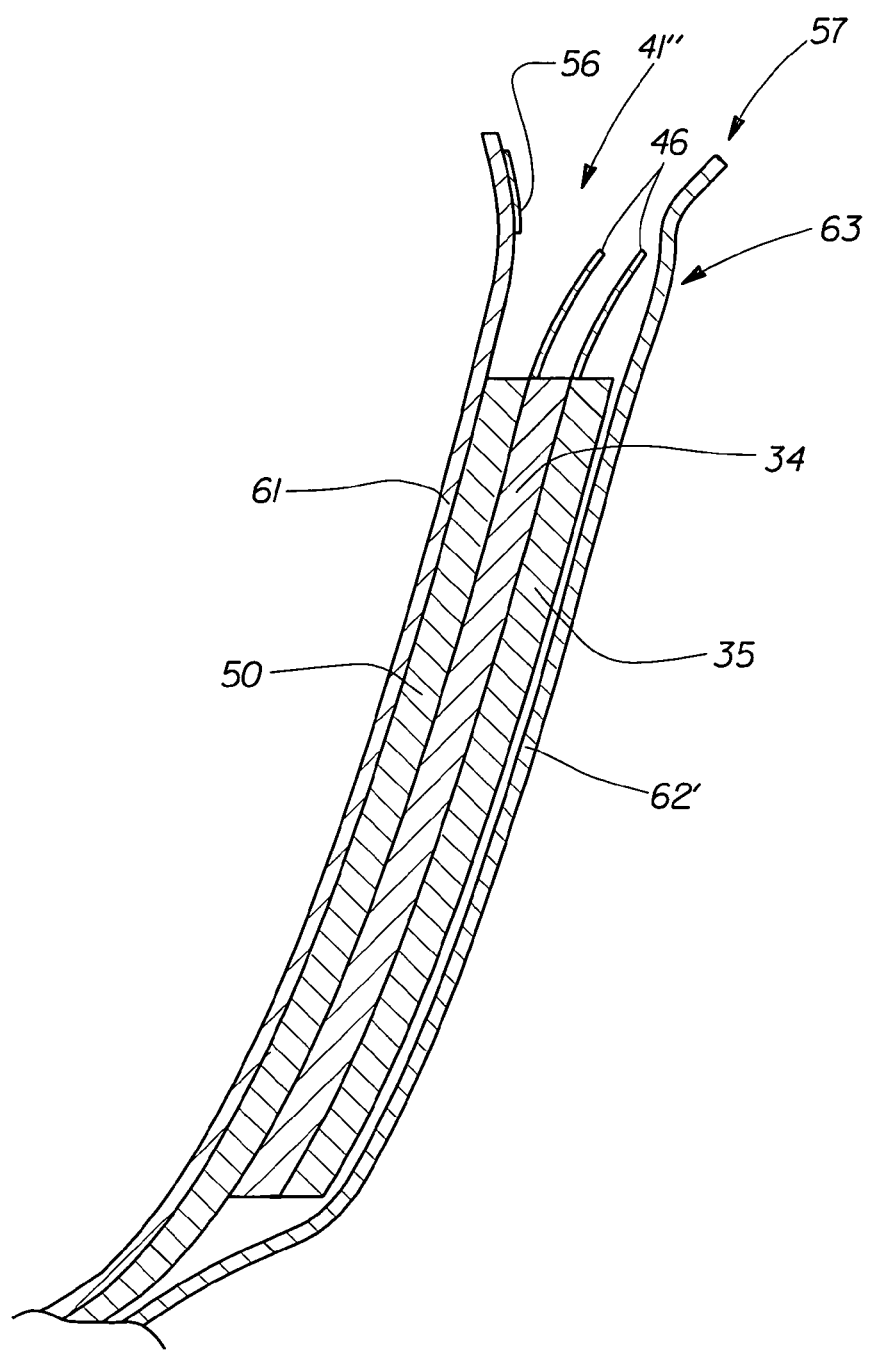
FIG. 8 is a cross-section depicting an additional alternative method of providing for a removable and replaceable absorbent core component of an absorbent article according to the present invention.

An alternative embodiment of an absorbent article of the present invention has a fluid impervious backsheet without any discontinuities forming an opening through the backsheet. As shown in cross-section in FIG. 8, access to removable absorbent core members, e.g., members 34 and 35, is provided by an opening 41" between a topsheet 61 and backsheet 62'. As more fully described below with reference to FIG. 10, a fluid pervious topsheet is often used in absorbent articles as the wearer-contacting portion of the article. In an article of the present invention, the topsheet 61 and backsheet 62' may be separable at predetermined areas of the periphery 57, near waistband region 63, either in the front, back, or both. FIG. 8 shows the topsheet and backsheet separated in an open position. The opening 41" formed by the separation of the topsheet and backsheet allows removal or replacement of absorbent core components and is preferably resealable to provide for substantial fluid impermeability. The opening may be made resealable, for example, with a suitable adhesive 56 known in the art.

Those skilled in the art will recognize additional embodiments of absorbent articles providing access to absorbent core components that do not depart from the scope of the present invention. For example, a back panel pocket may be formed integrally with a backsheet by plastically deforming the backsheet in the area of the backsheet adjacent to the front and back panels. A backsheet discontinuity in the form of an opening may then be made, by die cut, for example, to allow access to front or back panels. A flap similar to flap 42 of FIG. 1 may be provided along with fastening means, to cover the opening in the backsheet.

Furthermore, it is contemplated that additional combinations of absorbent core components or members, placement and absorptive characteristics may be used, with desired functional requirements influencing the ultimate design without departing from the scope of the present invention. In particular, the absorbent core may be configured as described below.

The Absorbent Core

Figure 9:
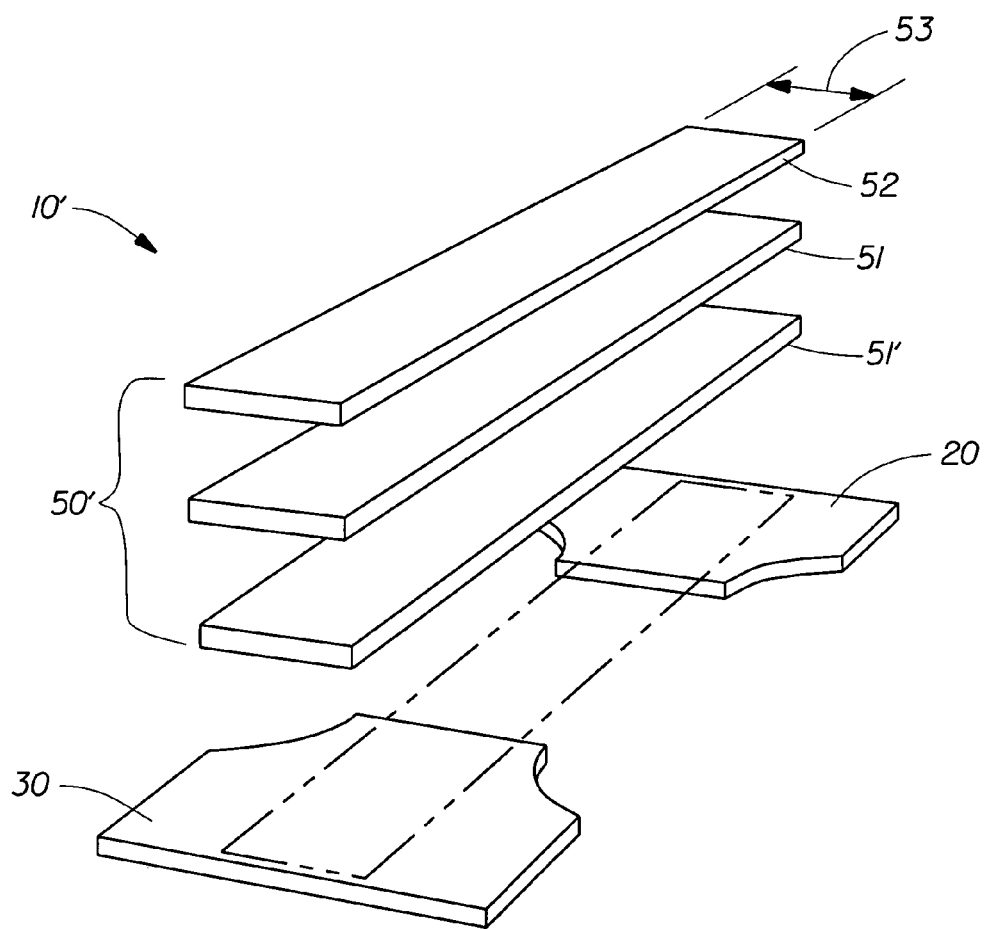
FIG. 9 is an exploded perspective view depicting the relationship between the elements of an embodiment of an absorbent core of the present invention.
Figure 11:
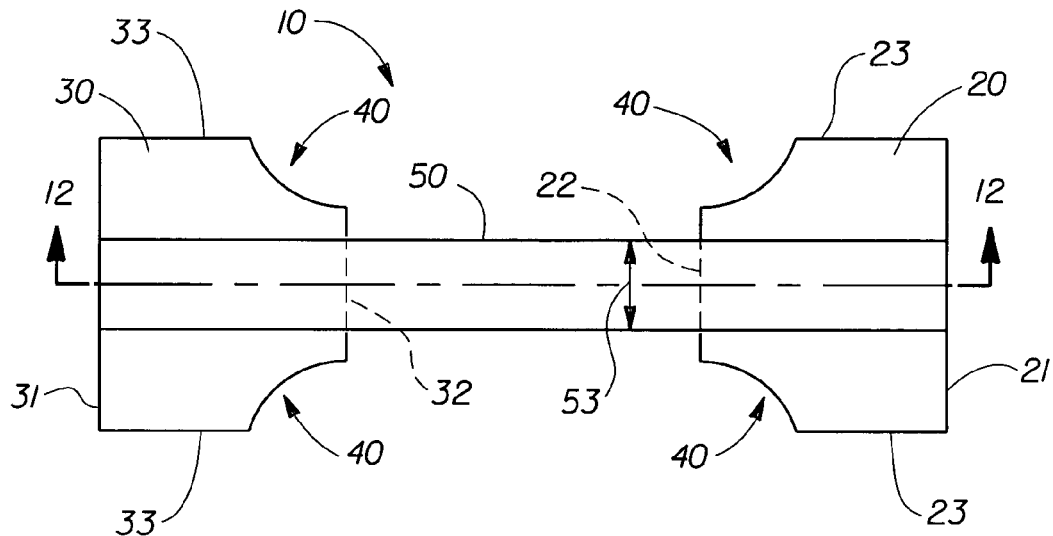
FIG. 11 shows a top view of an embodiment of an absorbent core useful in an absorbent article according to the present invention.

FIG. 9 shows an exploded perspective view depicting the elements of an embodiment of a shaped absorbent core 10' such as may be used in an absorbent article according to the present invention, for example, in a disposable diaper. As depicted in FIGS. 1 and 11, the absorbent core 10 comprises a front panel 20 and a back panel 30, both made of absorbent material, preferably material suitable for fluid storage/redistribution. The front panel 20 has an outer front end 21, an inner front end 22, and a pair of sides 23. Similarly, the back panel 30 has an outer end 31, an inner back end 32, and a pair of sides 33. The front panel 20 has cut-out areas 40 at the intersection of the sides 23, and the inner front end 22. Similarly, the back panel 30 has cut-out areas 40 at the intersection of the sides 33, and the inner back end 32. The cut-out areas 40, or notched portions, join the sides and the inner ends such that the resulting widths of the inner ends 22 and 32 are narrower than that of the outer ends 21 and 31, respectively. By "notched" is meant that instead of a side and end meeting at a generally right angle, some amount of material is removed from the corner to produce an additional edge portion joining the side and end. The additional edge portion of notch 40 may be generally straight, but in a preferred embodiment it is generally arcuate, as depicted in FIG. 11. It is also contemplated that the notch may have generally straight sides, with the limiting example resulting in a back or front panel being substantially trapezoidal-shaped.

In a generally-flat, unfolded state, the front panel and back panel are positioned such that the inner front end of the front panel is opposed to and spaced from the inner back end of the back panel as shown in FIGS. 9–13. The distance between the front and back panels may be varied as necessary. In general the distance will increase as the crotch length increases with the size of the absorbent article.

Figure 10:
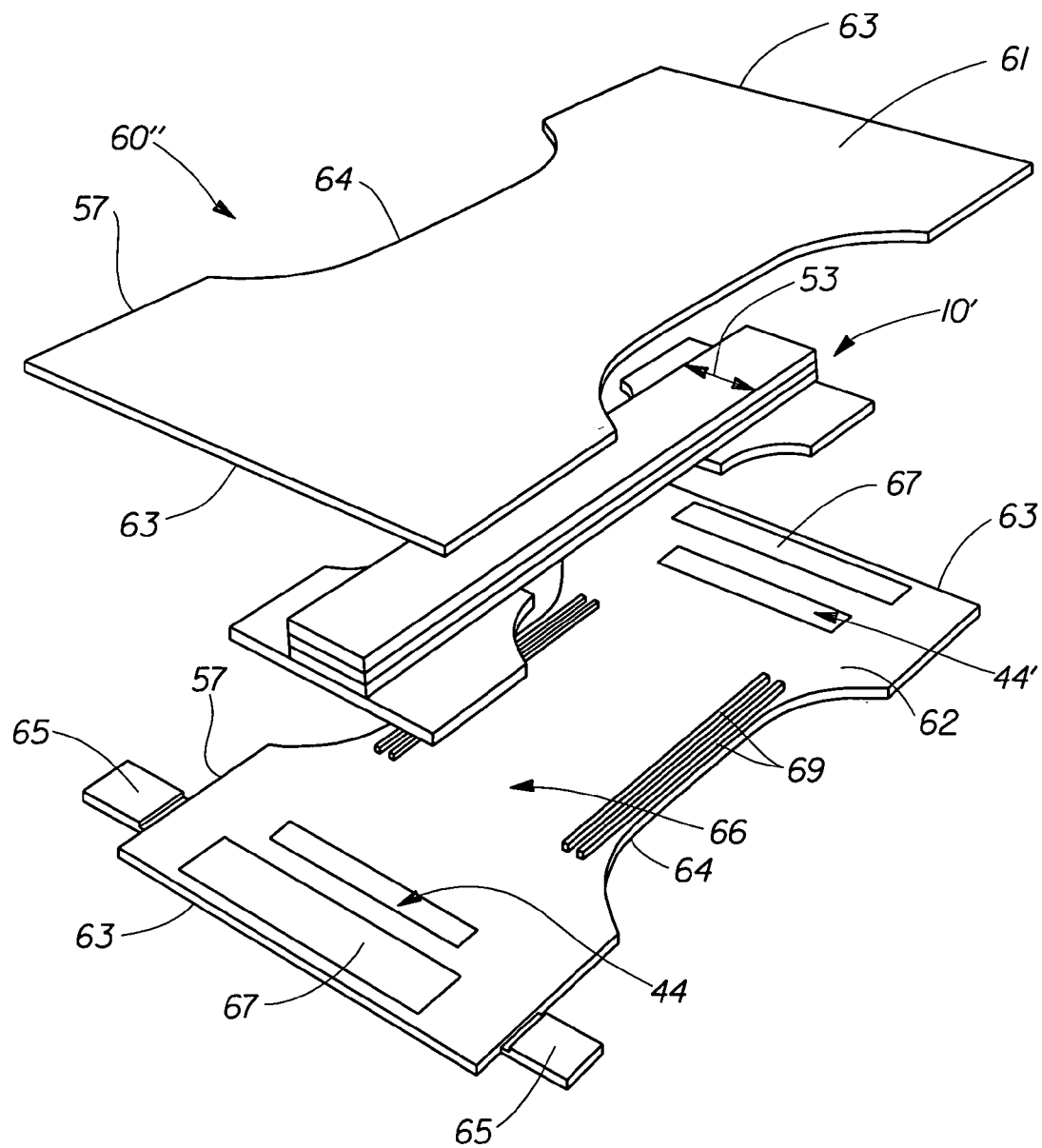
FIG. 10 is an exploded perspective view depicting an embodiment of an absorbent article according to the present invention.

The center section is preferably generally rectilinear. By "generally rectilinear" is meant that preferably the center section is of constant width along its length. In general, however, the center section need only span and overlap the front and back panels, and may have a varying width along its length. When made by the method of the present invention, the center section is generally rectilinear and extends from about the outer front end of the front panel, to about the outer back end of the back panel, as shown in FIG. 10. In use, however, the center section need only be in fluid communication with the front and back panels, preferably by overlapping in a layered relationship, and may not extend to the outer front end or the outer back end.

The generally rectilinear center section may comprise multiple strips of absorbent material, each having individual fluid acquisition, acquisition/distribution or storage/redistribution characteristics, as well as individual shape, width, length and thickness characteristics. For example, in a preferred embodiment shown in FIG. 9, two relatively thin, flexible, resilient, polymeric foam strips 51 and 51' are preferably made from the same storage/redistribution material as the front and back panels 20 and 30. The strips 51 and 51' and front and back panels 20 and 30, having similar absorptive characteristics and being in fluid communication act as primary storage/redistribution members.

In a preferred embodiment generally rectilinear strip 52 comprises a relatively-thin, flexible, resilient, polymeric foam material having greater fluid acquisition or acquisition/distribution characteristics than strips 51 and 51', thereby tending to quickly acquire and partition body exudates for more rapid absorption into storage/redistribution layers 51 and 51' and front and back panels 20 and 30.

As described with reference to FIGS. 1–4, the fluid absorbent core can be utilized in disposable products which are capable of absorbing significant quantities of body fluids, such as urine, perspiration, menses, and water in body wastes. Such articles may be prepared in the form of disposable diapers, adult incontinence briefs, and the like in general these absorbent articles comprise three basic structural components: a substantially fluid impervious backsheet; an absorbent core; and a substantially fluid pervious topsheet.

As shown in FIG. 10, the backsheet 62 of an embodiment of an absorbent article of the 17 present invention is generally made of substantially liquid impervious material, but it is not continuous. In particular, a discontinuity in backsheet 62 forms an aperture 44. Adjacent backsheet 62 is disposed an absorbent core 10' which may itself comprise one or more absorbent components in distinct layers. Adjacent absorbent core 10' and preferably joined to the backsheet is a fluid pervious topsheet 61. Preferably, topsheet 61 and backsheet 62 are joined directly at the absorbent article's periphery by adhesive or other attachment means known in the art. Topsheet 61 may also be adhered to the absorbent core. It is also contemplated that topsheet 61 may be unitary with one or more absorbent core components, thereby essentially reducing the absorbent article to two basic structural components: an absorbent core having core components with an integral topsheet, and a backsheet.

FIG. 10 shows an exploded perspective view of an absorbent core 10' as contemplated for use in a disposable diaper according to the present invention. It should be understood, however, that the absorbent core 10' shown is also useful for other absorbent articles such as incontinent briefs, incontinent pads, training pants, and the like. The diaper depicted in FIG. 10 is a simplified absorbent article that could represent a diaper prior to its being placed on a wearer. It should be understood, however, that the present invention is not limited to the particular type or configuration of diaper shown in FIG. 10.

In the incorporated references, the entire absorbent core is typically non-removably disposed in the absorbent article. However, as described throughout this disclosure, specific components of the multi-piece absorbent core are removable and replaceable in absorbent articles of the present invention. For instance, the front panel 20 and/or the back panel 30 may be removable and replaceable, while another component, such as the center section 50, may be non-removably disposed in any of the previously known configurations and thereby be made non-removable from the absorbent article. Thus, absorbent articles of the present invention have both non-removable absorbent core components and absorbent core components that are removable and replaceable.

As described in the incorporated references, components of the absorbent core may be made non-removable from the chassis by being secured, attached, affixed, and/or sandwiched to or in the chassis. For example, as described in the Buell '003 patent, an absorbent core component can be rendered immobile by, for example, bonding the backsheet and the absorbent core component together, bonding the absorbent core component to a topsheet and the topsheet to the backsheet, or tightly sandwiching the absorbent core component between a topsheet and the backsheet. Also, as described in the Lawson '278 patent, an absorbent core component may be superimposed on the backsheet and attached thereto by attachment means such as those well known in the art. For example, the absorbent core component may be secured to the backsheet by a uniform continuous layer of adhesive, a patterned layer of adhesive, or an array of separate lines or spots of adhesive. In some exemplary embodiments, an absorbent core component may be affixed in the crotch area of the chassis, as described in the DesMarais et al. '345 patent. Similarly, as described in the Osborn '264 patent, an absorbent core component may be attached over the core's upper or lower major surfaces, respectively, to adjacent members such as the topsheet and the backsheet by any of the means well known in the art, such as by spray-gluing or lines or spots of adhesive.

Disposable diaper 60" is shown in its uncontracted state (i.e., with generally all the elastic induced contraction removed) to more clearly show the construction of the diaper. The diaper may comprise a substantially liquid pervious topsheet 61; a substantially liquid impervious backsheet 62 joined with the topsheet 61; and an absorbent core 10' positioned between topsheet 61 and backsheet 62. Additional structural features such as elastic members and fastening means for securing the diaper in place upon a wearer (such as tape tab fasteners) may also be included.

While the topsheet, the backsheet, and the absorbent core can be assembled in a variety of well known configurations, a preferred diaper configuration is described generally in U.S. Pat. No. 3,860,003 to Buell, issued Jan. 14, 1975, which is hereby incorporated herein by reference. Alternatively preferred configurations for disposable diapers herein are also disclosed in U.S. Pat. No. 4,808,178 to Aziz et al., issued Feb. 28, 1989; U.S. Pat. No. 4,695,278 to Lawson, issued Sep. 22, 1987; and U.S. Pat. No. 4,816,025 to Foreman, issued Mar. 28, 1989, all of which are hereby incorporated herein by reference.

FIG. 10 shows a preferred embodiment of the diaper in which the topsheet and the backsheet are co-extensive and have length and width dimensions generally larger than those of the absorbent core. The topsheet is joined with and superimposed on the backsheet thereby forming the periphery of the diaper. The periphery defines the outer perimeter or the edges of the diaper.

The topsheet is compliant, soft feeling, and non-irritating to the wearer's skin. Further, the topsheet is liquid pervious permitting liquids to readily penetrate through its thickness. A suitable topsheet can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet is made of a hydrophobic material to isolate the wearer's skin from liquids in the absorbent core. A particularly preferred topsheet comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which can be used to manufacture the topsheet. For example, the topsheet can be woven, nonwoven, spunbonded, carded, or the like. A preferred topsheet is carded, and thermally bonded by means well known to those skilled in the fabrics art. Preferably, the topsheet has a weight from about 18 to about 25 grams per square meter, a minimum dry tensile strength of at least about 400 grams per centimeter in the machine direction, and a wet tensile strength of at least about 55 grams per centimeter in the cross-machine direction.

While it is preferred to have a topsheet as the material nearest the wearer's skin, it is not necessary. It is contemplated that a suitable absorbent core configuration could be used without a topsheet and still produce desirable results such as comfort and absorbency as well as simplicity in manufacturing and material cost savings. For example, the body-side surface of the absorbent article itself could be made of liquid pervious, soft, compliant, non-irritating materials that substitute for a separate topsheet. Such an absorbent core would only need to be used in combination with a backsheet to provide for comfort and absorbency in an absorbent article.

The backsheet is made of a material substantially impervious to liquids and is preferably manufactured from a thin plastic film, although other flexible liquid impervious materials may also be used. Backsheet prevents the exudates absorbed and contained in the absorbent core from wetting articles which contact the diaper such as bed sheets and undergarments. Preferably, the backsheet is polyethylene film having a thickness from about 0.012 mm (0.5 mil) to about 0.051 centimeters (2.0 mils), although other flexible, liquid impervious materials can be used. As used herein, the term "flexible" refers to materials which are compliant and which will readily conform to the general shape and contours of the wearer's body. The polyethylene film of the backsheet may be used for flap 42 as well.

A suitable polyethylene film is manufactured by Monsanto Chemical Corporation and marketed in the trade as Film No. 8020. The backsheet is preferably embossed and/or matte finished to provide a more clothlike appearance. Further, the backsheet may be "breathable," permitting vapors to escape from the absorbent core while still preventing exudates from passing through the backsheet. It is contemplated that a backsheet that is highly breathable but substantially impervious to liquid may be desirable for certain absorbent articles.

The size of the backsheet is dictated by the size of the absorbent core and the exact diaper design selected. In a preferred embodiment, the backsheet has a modified hourglass-shape extending beyond the absorbent core a minimum distance of at least about 1.3 centimeters to at least about 2.5 centimeters (about 0.5 to about 1.0 inch) around the entire diaper periphery. Additionally, according to the present invention more fully described below, the backsheet may have at least one aperture providing access through the backsheet to a portion of the absorbent core.

The topsheet and the backsheet are joined together in any suitable manner. As used herein, the term "joined" encompasses configurations whereby the topsheet is directly joined to the backsheet by affixing the topsheet directly to the backsheet, and configurations whereby the topsheet is indirectly joined to the backsheet by affixing the topsheet to intermediate members which in turn are affixed to the backsheet. In a preferred embodiment, the topsheet and the backsheet are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet to the backsheet.

Tape tab fasteners 65 are typically applied to the waistband region 63 of the diaper to provide a fastening means for holding the diaper on the wearer. The tape tab fasteners 65 depicted are representative only. The tape tab fasteners can be any of those well known in the art, such as the fastening tape disclosed in U.S. Pat. No. 3,848,594 (Buell), issued Nov. 19, 1974, which is hereby incorporated herein by reference. These tape tab fasteners or other diaper fastening means are typically applied near the corers of the diaper 60.

Elastic members 69 are disposed adjacent the periphery of the diaper, preferably along each longitudinal edge 64, so that the elastic members tend to draw and hold the diaper 60 against the legs of the wearer. Additionally, elastic members 67 can be disposed adjacent either or both of the waistband regions 63 of the diaper to provide a waistband as well as or rather than leg cuffs. For example, a suitable waistband is disclosed in U.S. Pat. No. 4,515,595 (Kievit et al.), issued May 7, 1985, which is hereby incorporated herein by reference. In addition, a method and apparatus suitable for manufacturing a disposable diaper having elastically contractible elastic members is described in U.S. Pat. No. 4,081,301 (Buell), issued Mar. 28, 1978, which is hereby incorporated herein by reference.

The elastic members are secured to the diaper in an elastically contractible condition so that in a normally unrestrained configuration, the elastic members effectively contract or gather the diaper. The elastic members can be secured in an elastically contractible condition in at least two ways. For example, the elastic members can be stretched and secured while the diaper is in an uncontracted condition. Alternatively, the diaper can be contracted, for example, by pleating, and the elastic members secured and connected to the diaper while the elastic members are in their unrelaxed or unstretched condition. The elastic members may extend along a portion of the length of the diaper. Alternatively, the elastic members can extend the entire length of the diaper, or any other length suitable to provide an elastically contractible line. The length of the elastic members is dictated by the diaper design.

In use, the diaper is applied to a wearer by positioning one waistband region under the wearer's back, and drawing the remainder of the diaper between the wearer's legs so that the other waistband region is positioned across the front of the wearer. The tape-tab 65 or other fasteners are then secured preferably to outwardly facing areas of the diaper, as shown in FIGS. 2 and 4, for example. In use, the disposable diapers or other absorbent articles of the present invention tend to more quickly and efficiently distribute and store liquids and to remain dry due to the high absorbent capacity of the fluid absorbent members. Disposable diapers incorporating the fluid absorbent members of the present invention can also be thinner and more flexible.

When used as an absorbent core in a disposable diaper 60, a preferred embodiment of the core 10' is positioned such that acquisition/distribution strip 52 is in fluid contact with topsheet 61, and serves to quickly acquire and partition body exudates from the wearer's body to the generally more absorptive storage/redistribution strips l' and front and back panels, 20 and 30. The front panel 20 generally corresponds to the portion of the disposable diaper worn in the front of the wearer, with the outer front end 21 being generally near the wearer's waist area. Similarly, the back panel 30 corresponds to the portion of the disposable diaper worn in the back of the wearer, with the outer back end 31 being generally near the wearer's waist area. Generally rectilinear center section has a width 53 corresponding to a suitable width for the crotch area 66 of a disposable diaper. As well, the length of generally rectilinear center section may be varied to provide a suitable fit for various wearer sizes.

FIG. 11 shows a top view of a shaped absorbent core 10, contemplated as one embodiment useful in an absorbent article of the present invention. As shown, the front and back panels 20 and 30, together with generally rectilinear center section 50, form generally an elongated hourglass shape suitable for use in a disposable diaper or similar absorbent article. In a preferred embodiment the width 53 of generally rectilinear center section 50 is suitable for comfortably fitting within the crotch area of the wearer when absorbent core 10 is incorporated into an absorbent article, such as a disposable diaper.

Figure 12:
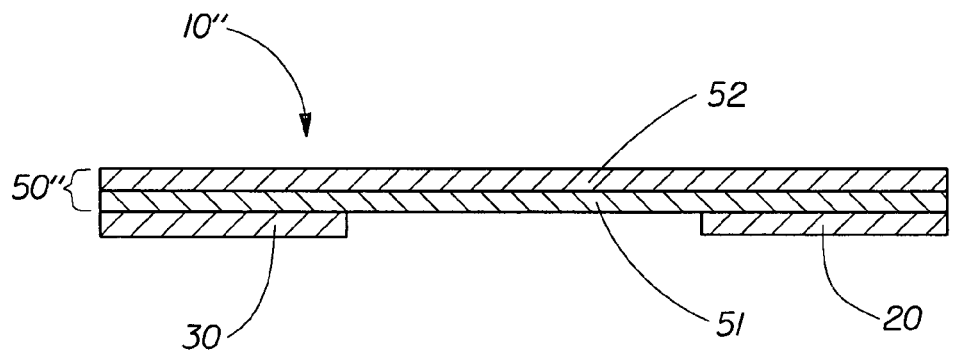
FIG. 12 is an elevational sectional view of the absorbent core of FIG. 11 taken along line 12—12.

The number and placement of strips 51 or 52 of generally rectilinear center section may be varied to achieve desired characteristics such as thinness, softness, flexibility, or beneficial fluid acquisition, distribution, and storage rates. For example, FIG. 12 shows in cross-section an embodiment using one acquisition/distribution strip 52 and one storage/redistribution strip 51 in center section 50", both placed over front and back storage/redistribution panels 20 and 30, resulting in a thin, flexible absorbent core 10". By "over" is meant the side of the absorbent core of the invention corresponding to the wearer's body when used in an absorbent article such as a disposable diaper.

The number of layers of the front and back panels may also be varied to achieve desired characteristics such as beneficial fluid acquisition and distribution rates, as well as capacity and storage rates. If more than one layer of absorbent material is used in the front or back panels, the panels are herein referred to as components, and the individual layers are herein referred to as members. For example, FIG.

Figure 13:
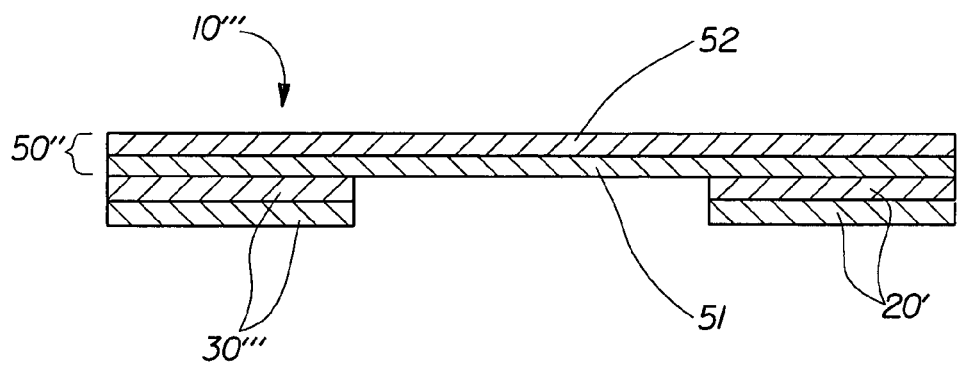
FIG. 13 shows an alternative embodiment of an absorbent core similar to that shown in FIGS. 11 and 12.

13 shows in cross-section an additional embodiment corresponding to the general top view of FIG. 11. FIG. 13 depicts two members of front and back panels 20' and 30'". As shown in FIG. 13, both back panel members may be placed under the center section. As described above with reference to FIGS. 5 and 6, the members of a multi-layer front or back panel may be separated by fluid impervious material with beneficial results.

In summary, the absorbent core comprises a plurality of discrete components, each component capable of having distinct fluid acquisition, acquisition/distribution, or storage/redistribution characteristics. In the context of the present invention, it should be noted that the term "fluid" means "liquid." So long as the acquisition, acquisition/distribution, and storage/redistribution components are in fluid communication with adjacent components, they may be positioned relative to one another in a wide variety of configurations. Representative materials suitable for use with the present invention will now be described in greater detail.

As described above, the absorbent core comprises a plurality of discrete components, each component may comprise discrete members, each capable of having distinct fluid acquisition, acquisition/distribution, or storage/redistribution characteristics. The components or members may be made of any absorbent material or combination of materials having enough structural integrity to be handled as a discrete unit. Typical materials known in the art may be used, such as fibrous nonwoven materials, fibrous wet-laid web materials, and combinations of fibrous materials having absorbent gelling materials dispersed upon or within the fibrous structure. If necessary, such fibrous nonwoven materials may be formed into a pouch, of material, being substantially enveloped by a fluid pervious web that provides the structural integrity for removal and replacement into the article of the present invention.

Particularly preferred absorbent materials for use as absorbent components or members are foam-based in nature. Polymeric foams which are suitable for use in the fluid acquisition component can in general be characterized as structures which result when a relatively monomer-free gas or relatively monomer-free liquid is dispersed as bubbles in a polymerizable monomer-containing liquid, followed by polymerization of the polymerizable monomers in the monomer-containing liquid which surrounds the bubbles. The resulting polymerized material. The cells themselves contain the relatively monomer-free gas or relatively monomer-free liquid, which, prior to polymerization, had formed the "bubbles" in the liquid.

Particularly suitable absorbent foams for absorbent articles such as diapers have been made from High Internal Phase Emulsions (hereafter referred to as "HIPE"). See, for example, U.S. Pat. No. 5,260,345 issued to DesMarais et al. on Nov. 9, 1993, U.S. Pat. No. 5,268,224 issued to DesMarais et al. on Dec. 7, 1993, and U.S. Pat. No. 5,563,179 issued to Stone et al. on Oct. 18, 1996, each of which is hereby incorporated herein by reference. These absorbent HIPE foams provide desirable fluid handling properties, including: (a) relatively good acquisition rates to quickly acquire gushes of urine; (b) relatively good wicking and fluid distribution characteristics to transport the imbibed urine or other body fluid away from the initial impingement zone and into the unused balance of the foam structure to allow for subsequent gushes of fluid to be accommodated, and (c) a relatively high storage capacity with a relatively high fluid capacity under load, i.e. under compressive forces.

HIPE absorbent foams are also sufficiently flexible and soft so as to provide a high degree of comfort to the wearer of an absorbent article; some can be made relatively thin until subsequently wetted by the absorbed body fluid. See also the aforementioned Young et al. '345 patent, and U.S. Pat. No. 5,318,554 issued to Young et al. on Jun. 7, 1994, which discloses absorbent cores having a fluid acquisition/distribution component that can be a hydrophilic, flexible, open-celled foam such as a melamine-formaldehyde for an (e.g., BASOTECT® made by BASF), and a fluid storage/redistribution component that is a HIPE-based absorbent foam.

Representative materials suitable for use with the present invention are not limited to HIPE foams, and will now be described in greater detail.

The Acquisition Component

One element of an absorbent core is a fluid acquisition component which comprises a porous absorbent structure that has certain fluid handling characteristics with respect to discharged aqueous body fluids, e.g., urine, passing onto and into this structure through, for example, the topsheet of an absorbent article as described above. Since such fluid is frequently discharged in gushes, the acquisition component must be able to quickly acquire, temporarily hold, and also preferably transport (or partition) fluid, e.g., by wicking or other mechanisms, from the point of initial fluid contact to other parts of the acquisition component for eventual absorption into the adjacent fluid acquisition/distribution or storage/redistribution components.

Any porous absorbent material which will imbibe and partition aqueous body fluids to acquisition/distribution or storage/redistribution components of the core may be used as the acquisition layer 52. One measure of the fluid acquisition effectiveness of the absorbent material used to form the acquisition component is the Fluid Acquisition Rate, whereby measurements are made of the time taken for aliquots of synthetic urine test liquid deposited onto the surface of an absorbent material to be absorbed into the internal structure of the absorbent material. Suitable fluid acquisition rates and test methods are disclosed generally in the aforementioned Young et al. '345 patent. Accordingly, the fluid acquisition component should be fashioned from an absorbent material which exhibits an initial Fluid Acquisition Rate of at least about 2 ml of synthetic urine per second. More preferably, the fluid acquisition component will comprise an absorbent material which exhibits an initial Fluid Acquisition Rate of at least about 6 ml of synthetic urine per second. The "initial" fluid Acquisition Rate is the time taken for the first aliquot of such test liquid to be absorbed into the absorbent material before such material already contains any of the synthetic urine test liquid.

Preferred absorbent materials for the acquisition component include synthetic fiber nonwoven materials, cellulosic nonwoven materials, and various synthetic/cellulosic nonwoven materials. A referred synthetic nonwoven material is disclosed in commonly assigned, U.S. Pat. No. 4,988,345 to Reising, issued Jan. 29, 1991, and U.S. Pat. No. 4,988,344 to Reising, issued Jan. 29, 1991, both of which are hereby incorporated herein by reference. The Reising acquisition layer comprises a first layer of hydrophilic fibrous material of lower average density than the other portions of the first layer so that it quickly acquires discharged liquids.

A preferred cellulosic nonwoven suitable for acquisition core components is formed from cellulose fibers that impart certain web and dry density characteristics to the absorbent core component. More specifically, the portions or regions of an absorbent core that acquire discharged bodily fluids will preferably have an average dry density of less than about 0.30 g/cc, and average density upon wetting with 1.0%, NaCl aqueous solution of less than about 0.20 g/cc, and an average dry basis weight from about 0.001 to about 0.10 g/cm$^2$. Preferred cellulosic nonwoven materials also comprise from about 50% to 100% chemically stiffened, twisted, and curled cellulosic fibers and from 0% to about 50% a binding means. Such a cellulosic nonwoven is disclosed in the aforementioned Young '345 patent, and commonly signed U.S. Pat. No. 5,531,728 to Lash, issued Jul. 2, 1996, which is hereby incorporated herein by reference.

The acquisition layer may be comprised of several different materials including nonwoven webs of synthetic fibers including polyester, polypropylene, or polyethylene, natural fibers including cotton or cellulose, blends of such fibers, or any equivalent materials or combinations of materials. Examples of such acquisition materials are more fully described in U.S. Pat. No. 4,950,264, to Osborn, issued on Aug. 21, 1990, which is hereby incorporated herein by reference. Cellulosic fibers, in addition to being chemically stiffened, may also be advantageously combined with high surface area fibers, such as eucalyptus fibers, as disclosed in commonly assigned, co-pending Ser. No. 08/686,076, to Seger et al., filed Jul. 24, 1996, the disclosure of which is hereby incorporated herein by reference. The chemically stiffened fibers and eucalyptus fibers may be coformed in a stratified manner with thermoplastic binding means or chemical binding means, as taught in the aforementioned Seger reference.

Preferable thermoplastic binder means, including preferable thermoplastic fibers, are disclosed in commonly assigned U.S. Pat. No. 5,549,589 to Homey et al., issued on Aug. 27, 1996, which is hereby incorporated herein by reference. Thermoplastic binding means may include any hot melt adhesive which can be melted at temperatures which will not extensively damage the cellulosic fibers. Once thermally set, the resulting nonwoven material exhibits wet/dry mechanical properties such as flexibility, resiliency and structural integrity such that it may be processed as rollstock in the method of the present invention.

If chemical binding means are used to give the nonwoven structural integrity, preferably the absorbent member will comprise between about 80% and about 95% of the chemically stiffened fibers, from about 3% to 20% of a high surface area fiber, and from 0% to about 5% of a chemical additive binding means. A presently preferred chemical additive binding means is the commercially available polyacrylamide-glyoxal resin marketed by Cytec Industries, West Patterson, N.J., under the trade name Parez™ 631 NC. Additional suitable fiber types and chemical additive binder means are disclosed in U.S. Pat. No. 5,800,416 issued to Seger et al. on Sep. 1, 1998, the disclosure of which is hereby incorporated by reference.

Other acquisition materials may be prepared by wetlaying in accordance with commonly assigned U.S. Pat. No. 5,217,445 to Young et al., issued Jun. 8, 1993, which is hereby incorporated herein by reference. In general, wetlaid webs can be made by depositing an aqueous slurry of fibers on to a foraminous forming wire, dewatering the wetlaid slurry to form a wet web, and drying the wet web. Further disclosure of particular wetlaying techniques suitable for forming an acquisition core component suitable for use in the present invention are disclosed in the aforementioned Young '345 patent. Besides acquiring body fluids rapidly, the absorbent acquisition component of the present invention should give up this fluid efficiently to other fluid acquisition/distribution or storage/redistribution components, including foam-based fluid storage components. Absorbent foams suitable for use as the acquisition component of the present invention combine relatively high capillary absorption pressures and capacity-per-weight properties (compared to conventional foams). Such foams are disclosed in U.S. Pat. No. 5,550,167 issued to Des Marais et al. on Aug. 27, 1996, which is hereby incorporated herein by reference.

The Fluid Acquisition/Distribution Components

The fluid acquisition/distribution components may comprise similar materials as the acquisition component, with more distributive characteristics. Since discharged aqueous body fluid, e.g., urine, frequently discharge in gushes, the acquisition/distribution component must be able to quickly acquire and must also preferably transport fluid, e.g., by wicking or other mechanisms, from the point of initial fluid contact to other parts of the acquisition/distribution component for eventual absorption into the adjacent fluid storage/redistribution component. Such materials are preferably polymeric foam materials having a greater degree of distributive capacity such that body exudates may more efficiently be transported from the acquisition zone to the storage components of the absorbent core.

Absorbent materials comprising the fluid acquisition/distribution component of the articles herein will preferably be suitably effective at transporting absorbed liquid from one part or region of the acquisition/distribution component to another. Such liquid transport will frequently arise by virtue of the propensity of the acquisition/distribution component absorbent material to wick liquid through its structure. Accordingly, one measure of the fluid distribution effectiveness of the absorbent material used to form the acquisition/distribution component relates to the ability of such absorbent material to vertically wick synthetic urine.

Vertical wicking effectiveness can be measured and quantified in a number of ways, but one typical indicator of vertical wicking performance is the height to which a vertically positioned test strip of absorbent material will wick synthetic urine from a reservoir within a specified period of time. For purposes of the present invention, this height, termed the Vertical Wicking Height, is determined by the procedure described in the aforementioned Young et al. '345 patent. The fluid acquisition/distribution component of the articles herein will preferably be formed from absorbent material which exhibits a 30-minute Vertical Wicking Height of at least about 5 cm. More preferably, the fluid acquisition/distribution component will comprise absorbent material which has a 30-minute Vertical Wicking Height of at least about 10 cm, and most preferably the absorbent material which exhibits a Vertical Wicking Height of 25 cm.

Any porous absorbent material which will imbibe and partition aqueous body fluids to the extent set forth hereinbefore in terms of Fluid Acquisition Rate and preferably Vertical Wicking Height may be utilized as, or as part of the fluid acquisition/distribution component of the absorbent articles disclosed herein. Frequently such absorbent material can be foam-based and/or fiber-based in nature.

A preferred embodiment utilizes an open-celled absorbent polymeric foam material that, in addition to functioning as an acquisition distribution component in an absorbent core, has improved desorption properties to allow other core components having higher absorption pressures than the desorption pressure of the acquisition/distribution foam to partition away fluid. In particular, absorbent foams useful in or as the fluid acquisition/distribution component we those which have a pore volume of from about 2 to 100 ml/g, a capillary suction specific surface area of from about 0.2 to 1 m$^2$/g; a cell size of from about 10 to 300 microns and a density of from about 0.01 to 0.5 g/cm$^3$, provided valued for these parameters are selected so that the absorbent foams exceed the aforementioned Vertical Wicking Rate minimum. The concepts of foam flexibility, hydrophilicity, pore volume, capillary suction, specific surface area, cell size, and density as relate to the present invention are described in greater detail in the aforementioned Young et al. '345 patent. Open-celled absorbent polymeric foam materials suitable for use as acquisition/distribution components in the present invention are described in the aforementioned Stone et al. '179 patent.

Other types of non-woven structures suitable for use as the fluid acquisition/distribution component include structures such as surfactant-treated bonded carded webs, webs of melt blown synthetic macrofibers or microfibers, pulp coformed webs, staple fiber coformed webs and the like. If non-woven fibrous absorbent structures are utilized in the present invention, such webs are preferably constructed essentially from hydrophilic chemically stiffened cellulosic fibers. Such cellulosic fibers are typically wood pulp fibers which have been stiffened with an intrafiber chemical stiffening agent and otherwise processed so they are formed into a twisted, curled configuration, as fully taught in the aforementioned Lash and Young et al. '345 patents, as well as the Seger '416 patent.

The Fluid Storage/Redistribution Components

An absorbent core suitable for use with the present invention comprises at least one, and preferable two, distinct fluid storage/redistribution core components. The fluid storage/redistribution core components act to store body exudates away from the wearers body so as to leave the wearer with a feeling of dryness and to prevent leakage. The storage/redistribution core components are maintained in fluid communication with the acquisition or acquisition/distribution layer(s) such that urine or other aqueous body fluids present in the acquisition/distribution component can be desorbed, being absorbed by the fluid storage/redistribution component(s).

Fibrous nonwoven materials as described above, particularly when combined with particulates of substantially water insoluble, absorbent hydrogel-forming polymer materials, may be useful as the fluid storage/redistribution component (s). Particularly useful are nonwoven materials containing absorbent gelling materials such as disclosed in U.S. Pat. No. 5,061,259 to Goldman et. al, issued Oct. 29, 1991, U.S. Pat. No. 4,654,039 to Brandt et al., issued Mar. 31, 1987 (reissued Apr. 19, 1988 as Re. 32,649), U.S. Pat. No. 4,666,983 to Tsubakimoto et al., issued May 19, 1987, and 4,625,001 to Tsubakimoto et al., issued Nov. 25, 1986, all of which are hereby incorporated herein by reference; absorbent macrostructures made from these absorbent gelling materials such as those disclosed in U.S. Pat. No. 5,102,597 to Roe et al., issued Apr. 7, 1992, and U.S. Pat. No. 5,324,561 to Rezai et al., issued Jun. 23, 1994, both of which are hereby incorporated herein by reference; absorbent gelling materials laminated between two tissue layers such as those disclosed in U.S. Pat. No. 4,260,443 to Lindsay et al., issued Apr. 7, 1981, U.S. Pat. No. 4,467,012 to Pedersen et al., issued Aug. 21, 1984, U.S. Pat. No. 4,715,918 to Lang, issued Dec. 29, 1987; U.S. Pat. No. 4,773,903 to Weisman et al., issued Sep. 27, 1988; 4,851,069 to Packard et al., issued Jul. 25, 1989; U.S. Pat. No. 4,923,454, to Seymour et al., issued May 8, 1990; to Osborn, issued Aug. 21, 1990; to Bernardin, issued Feb. 19, 1991; 1 Bernardin, issued Apr. 23, 1991; U.S. Pat. No. 5,009,653 to Osborn, issued Apr. 23, 1991; U.S. Pat. No. 5,128,082 to Makoui, Jul. 7, 1992; U.S. Pat. No. 5,149,335 to Kellenberger et al., issued Sep. 22, 1992; and U.S. Pat. No. 5,176,668 to Bernardin, issued Jan. 5, 1993, all of which are hereby incorporated herein by reference.

A preferred fluid storage/redistribution component of the absorbent core comprises cohesive sheets made from particulates of substantially water insoluble, absorbent hydrogel-forming polymer materials. Sheets may be made by layering predetermined amounts of the hydrogel-forming materials with cross-linking agents and ring. A preferred material of this type is disclosed in commonly assigned U.S. Pat. No. 5,324,561 to Rezai et al., issued Jun. 28, 1994, which is hereby incorporated herein by reference.

The most preferred fluid storage/redistribution component materials comprise collapsible polymeric foam materials that, upon contact with aqueous fluids (in particular aqueous body fluids such as urine), may expand and absorb these fluids. These absorbent polymeric foam materials comprise a hydrophilic, flexible, nonionic polymeric foam structure of interconnected open-cells as disclosed in U.S. Pat. No. 5,387,207 issued to Dyer et al. on Feb. 7, 1995, and U.S. Pat. No. 5,650,222 issued to DesMarais et al. on Jul. 22, 1997, both of which are hereby incorporated by reference. Other suitable polymeric absorbent foam materials, material characteristics, and characterizing tests are disclosed and taught in the aforementioned Young et al. '345 patent.

Polymeric foams materials suitable for use as a storage/redistribution component in an article of the present invention should have high capillary absorption pressures, also known as capillary suction, to effectively desorb adjacent acquisition and acquisition/distribution components. Capillary absorption pressures can be measured using a vertical wicking absorbent capacity test as described in detail in the TEST METHODS section of the aforementioned Dyer et al. '207 patent. Data from the vertical wicking absorbent capacity test provides the curve from which the capillary absorption pressure is determined. Preferred absorbent foams for use in an article of the present invention have capillary absorption pressures of from about 3 to about 20 cm. Particularly preferred absorbent foams have capillary absorption pressures of from about 3 to about 15 cm.

The collapsible polymeric foam storage/redistribution component may utilize low density (when expanded) absorbent foams. For a given expanded thickness, these lower density foams are thinner in their collapsed state than prior absorbent HIPE foams. These lower density foams more efficiently utilize the available polymer material and as a result provide an economically attractive means for achieving thinner absorbent cores for absorbent articles such as diapers, pull-up training pants, adult incontinence pads or briefs, sanitary napkins, and the like. This is achieved while retaining desired capillary absorption pressures, dryness, and mechanical properties.

The Method and Apparatus for Making Shaped Absorbent Cores

Figure 14:
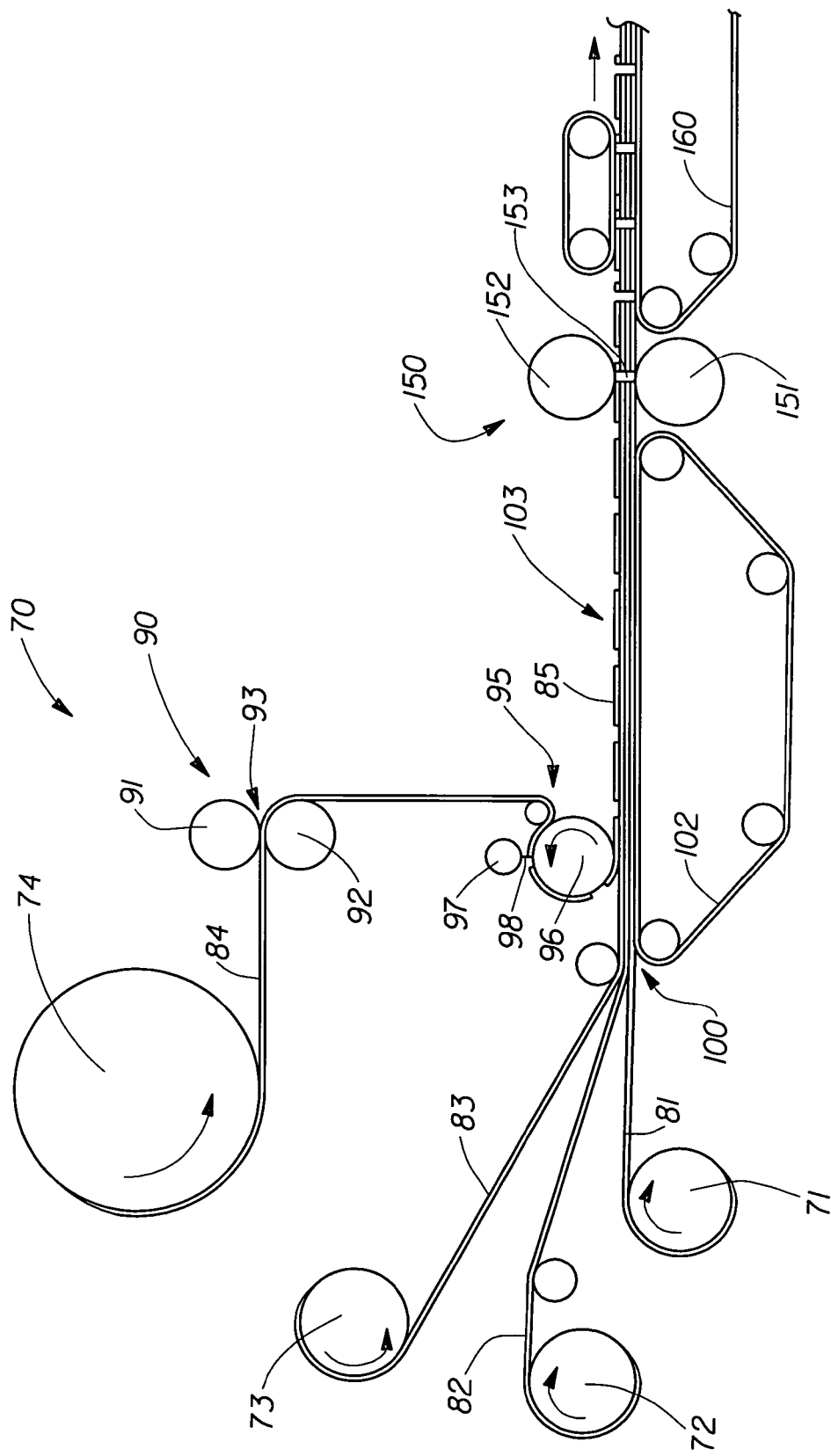
FIG. 14 schematically shows an apparatus for forming one embodiment of the shaped absorbent cores according to the method of the present invention.

A preferred method of making the shaped absorbent core suitable for use with the present invention is now described with reference to FIGS. 14–19. FIG. 14 schematically shows a representative apparatus 70 suitable for accomplishing the method of forming the absorbent core components of the preferred embodiment of the present invention as depicted in FIGS. 9 and 10. The method depicted in FIG. 14 and described in detail below can be easily modified to produce absorbent cores comprising different combinations and placement of absorbent members, such as those depicted in FIGS. 12 and 13. Representative modifications are shown schematically in FIG. 15 and, unless otherwise disclosed, can be understood with reference to the description of the method of FIG. 14 since like numerals identify like elements. The method is not limited to nonwoven web materials or absorbent polymeric foam materials, but is suitable for use with any generally absorbent material formed into webs, either nonwoven or woven, fibrous or polymeric, as known in the art that may be supplied on rollstock and have sufficient integrity to be processed by the method disclosed.

A first relatively narrow rectilinear web 81 is unwound from a supply roll 71. Web 81 has a width generally corresponding to width 53 of the generally rectilinear center section 50'. Web 81 comprises a material suitable for use as an acquisition/distribution layer 52 of the preferred embodiment 0''' as shown in FIGS. 9 and 10. Web 81 is guided through entry point 100 onto a conveyor 102 where it is positioned for further processing as described below.

In a preferred embodiment, second and third relatively narrow rectilinear webs 82 and 83, comprised of a material suitable for acquisition/distribution or storage/redistribution of aqueous fluid, are unwound from supply rolls 72 and 73, respectively. Webs 82 and 83 correspond to storage/redistribution layers 51 and 51' of FIGS. 9 and 10 and may have a width generally corresponding to width 53 of the center section 50'. Webs 82 and 83 are guided through entry point 100 onto a conveyor 102 where they are positioned in layers upon web 81 for further processing as described below.

A relatively wide continuous rectilinear web 84 of absorbent material having a longitudinal axis and lateral sides is unwound from a supply roll 74. In a preferred embodiment, web 84 is suitable for use as a storage/redistribution member of the absorbent core 10, and is of a width suitable for forming into the front panel 20 and back panel 30 shown in FIGS. 9 and 10. The lateral sides of web 84 generally correspond to the sides 23 and 33 depicted in FIG. 11.

Figure 16:
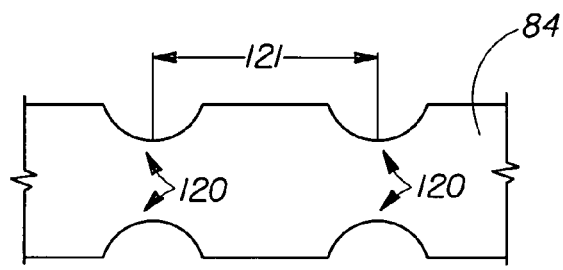
FIG. 16 is a plan view of a relatively wide continuous rectilinear web after notching.

Web 84 is guided from roll 74 to a notching apparatus 90. Notching apparatus 90 preferably comprises two nip rollers 91 and 92 through which web 84 is fed. As web 34 is fed through nip 93 of rollers 91 and 92, cutting blades (not shown) on roller 91 notch out substantially arcuate portions from opposing sides of web 84 so that as web 84 leaves the notching apparatus 90, it appears as shown in FIG. 16. FIG. 16 shows the continuous rectilinear web 84 with substantially arcuate notches 120 at spaced intervals 121 corresponding to the placement of the cutting blades on roller 91, shown in FIG. 14.

Figure 17:
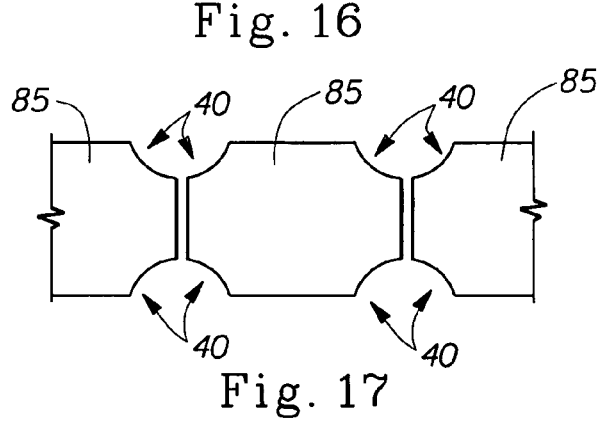
FIG. 17 is a plan view of a relatively wide continuous rectilinear web after a first cutting operation to produce discrete sections.

The continuous rectilinear web 84, notched as shown in FIG. 16, is next fed into a first slip and cut assembly 95 for making cuts transverse to the longitudinal axis that sever the rectilinear web 84 into discrete sections 85, and to separate the discrete sections as shown in FIG. 17. Web 84 is guided onto rotating drum 96 that serves as a platen. Once in contact with the surface of rotating drum 96, and prior to being cut into discrete sections, web 84 is moving at a speed less than that of the surface of the drum and slips relative to the surface of the drum 96 under light vacuum applied through perforations in the surface of the drum. Once web 84 is cut into discrete sections 85, a somewhat higher vacuum is applied so that severed sections 85 remain in contact with the rotating drum 96, moving at the same speed as the surface of the drum in a spaced apart relationship. Cutting roller 97 rotates in concert with rotating drum 96, the diameter of cutting roller 97 being such that a cutting blade 98 attached to cutting roller 97 severs rectilinear web 84 at the spaced intervals 121 of FIG. 16, forming the discrete sections 85. As shown in FIG. 17, the discrete sections 85 can best be described as generally rectangular in shape with notched corners 40, corresponding to the notches 40 of FIG. 11.

The rotating drum 96 is positioned such that upon rotation, discrete sections 85 are brought into contact with layer 83 moving upon conveyor 102. The vacuum arrangement in rotating drum 96 is such that at the position of contact with layer 83, discrete section 85 is released from rotating drum 96 and continues to be carried upon layer 83 by conveyor 102. The linear velocity of conveyor 102 is generally equal to the tangential linear velocity of rotating drum 96, so discrete sections 85 are deposited in a spaced relationship onto layer 83, as depicted in FIG. 18.

Figure 18:
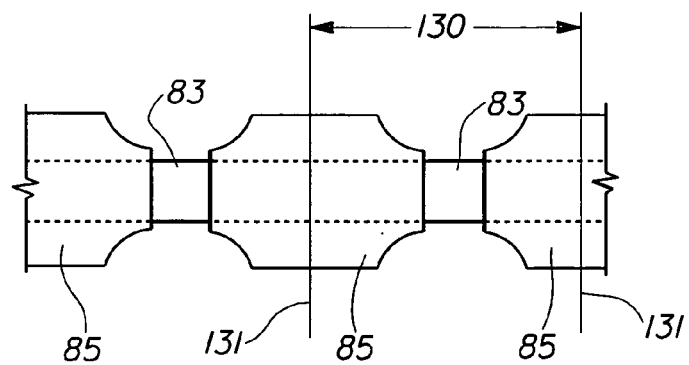
FIG. 18 is a plan view of the relatively wide rectilinear web discrete sections layered in spaced relationship on relatively narrow continuous rectilinear webs.

FIG. 18 shows in plan view the material being carried by conveyor 102 at, for example, point 103 in FIG. 14. Layer 83, and layers 82 and 81 below (not shown), form continuous rectilinear webs under discrete sections 85 laying in a spaced apart relationship. Discrete sections 85 are spaced apart at spaced intervals 130, corresponding generally with the distance between transverse centerlines 131 of adjacent discrete sections 85.

The material being carried on conveyor 102 is fed into a second slip and cut assembly 150 for making transverse cuts severing all the layers of material. Cutting roller 152 has a diameter corresponding generally to the distance between the transverse centerlines 131 of discrete sections 85 as shown in FIG. 18. Roller 151 serves as a platen for a cutting blade 153 attached to cutting roller 152. Cutting blade 153 completely severs the layers at or near transverse centerlines 131 of discrete sections 85. Upon exiting the second slip and cut assembly 150, the absorbent material has been formed into the individual absorbent cores 10' of the present invention. Various known methods may be used to separate the individual absorbent cores, such as by varying the relative speeds of conveyors 102 and 160. The individual absorbent cores are carried by conveyor 160 for further processing into absorbent articles, if necessary, and appear on conveyor 160 in plan view as shown in FIG. 19.

Figure 19:
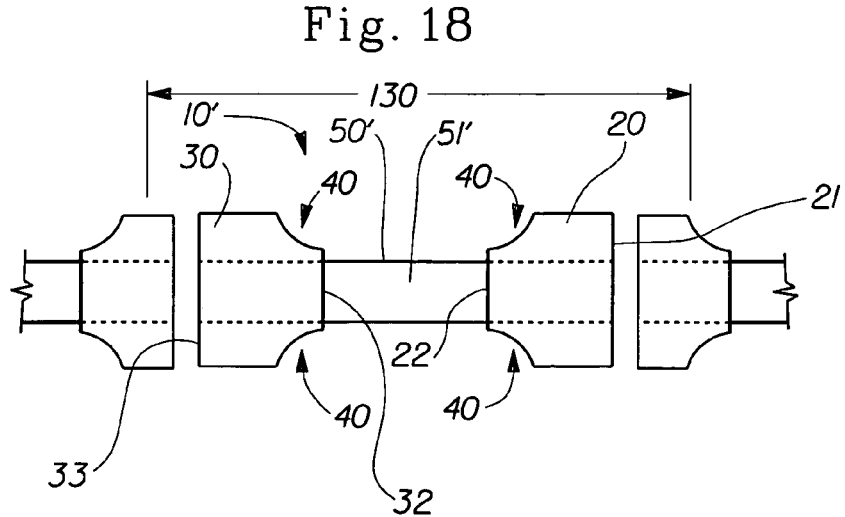
FIG. 19 is a plan view of finished shaped absorbent cores of the present invention as produced by a method of the present invention.

As shown in FIG. 19, it is not necessary for the length of front panel 20 measured from outer front end 21 to inner front end 22 to equal the length of the back panel 30 measured from its outer back end 31 to its inner back end 32. The position of the layered material on conveyor 102 in relation to the second slip and cut assembly 150 determines the relative lengths of front panel 20 and back panel 30. In a preferred embodiment of the present invention the back panel 30 is longer than the front panel 20 as depicted in FIG. 19. Such a configuration lends itself to a better fit when the absorbent core is used in a disposable diaper.

Figure 15:
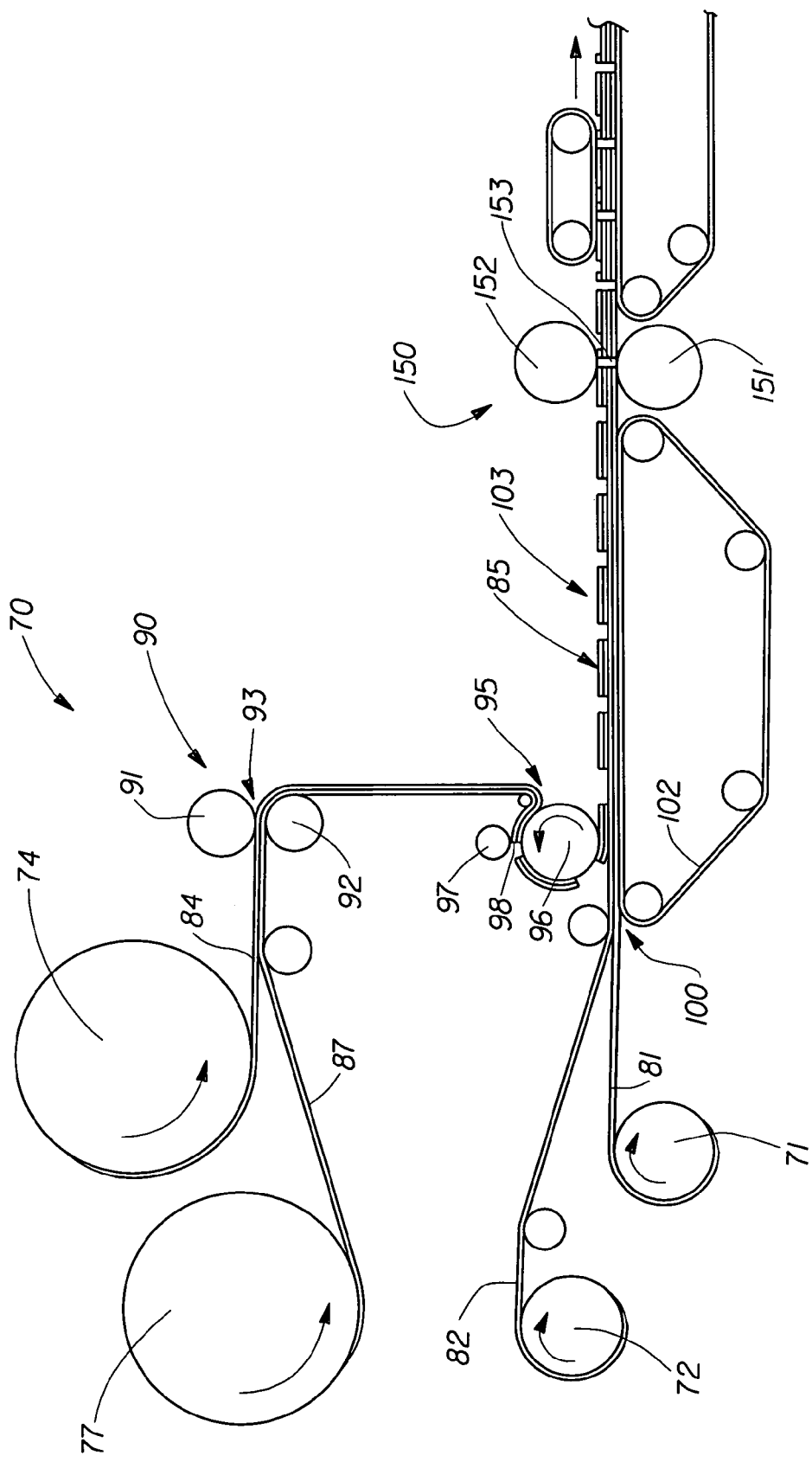
FIG. 15 schematically shows an apparatus for forming another embodiment of the shaped absorbent cores according to the method of the present invention.

As shown in FIGS. 14 and 15, the length of interval 130 may be varied to produce the desired length of center section. It is desirable to be able to vary the length of center section of an absorbent core for use in disposable diapers to accommodate the difference in sizes of children or adults using such diapers.

FIG. 15 shows a representative method for forming the absorbent core 10''' as depicted in FIG. 13. In this embodiment, an additional relatively wide continuous rectilinear web 87 of absorbent material having a longitudinal axis and lateral sides is unwound from a supply roll 77 and is guided into contact and alignment with web 84 prior to entry into notcher 90. Webs 84 and 87 may be adhered together by known methods to facilitate proper alignment throughout the remainder of the process, particularly after being processed by slip and cut assembly 95.

The method disclosed provides a number of significant benefits. For example, the method generates significantly less scrap than would a typical method of forming a one-piece shaped absorbent core. Also, the method provides for efficient supplying of webs of absorbent materials from rollstock, especially foam, from which the panels and rectilinear strips are made. One advantage of such a process is a longer web roll life. For example, the narrower webs of absorbent material used to make the rectilinear strips can be spool wound for significantly longer roll life. A third benefit of the method disclosed is greater control over certain processing variables, such as placement of core components in proper operating relationship. For example, because the wider web of absorbent material is notched and severed at the point the front and back panels are made, it is significantly easier to register the notched/severed panels in the appropriate relationship with the narrower rectilinear strip(s) to make the composite absorbent core.

While particular embodiments of the present invention have been illustrated and described, it would be obvious to those skilled in the art that various other changes and modification can be made without departing from the spirit and scope of the present invention. The foregoing is therefore intended to cover in the appended claims all such changes and modifications that are within the scope of the present invention.

What is claimed is:

1. A disposable absorbent article, the article having a first waist region, a second waist region, and a crotch region positioned between the first waist region and the second waist region, the absorbent article further comprising:
    a backsheet joined to a fluid pervious topsheet, the backsheet comprising a web and being substantially liquid impervious except at a first discontinuity in the web; and
    an absorbent core disposed between the topsheet and the backsheet, the absorbent core comprising absorbent core components
    wherein the absorbent core component comprise a multilayered first absorbent core component non-removably disposed in at least the crotch region and has an acquisition layer and an acquisition/distribution layer, and at least one removable second absorbent core component removably disposed in the first waist region and is in fluid communication with the first absorbent core component, and
    wherein the backsheet further comprises first access means for providing access to the removable second absorbent core component through the backsheet so that the removable second absorbent core component may be removed from the absorbent article through the backsheet without having to remove the absorbent article from a wearer, the first access means comprising the first discontinuity in the web, the first discontinuity being positioned in the first waist region, a first recloseable flap secured over the first discontinuity, and a first fastener for recloseably joining the first flap to the remainder of the backsheet.

2. The disposable absorbent article of claim 1, wherein the acquisition and acquisition/distribution layers of the fist absorbent core component comprise fibrous nonwoven materials, fibrous wet-laid web materials, open-celled polymeric foam materials, or combinations thereof.

3. The disposable absorbent article of claim 2, wherein the acquisition and acquisition/distribution layers of the first absorbent core component comprise fibrous nonwoven materials and open-celled polymeric foam materials.

4. The disposable absorbent article of claim 2, wherein the fibrous nonwoven materials of the acquisition and acquisition/distribution layers are polyester fiber materials, polyethylene fiber materials, polypropylene fiber materials, cotton fiber materials, cellulose fiber materials, chemically stiffened cellulose fiber materials, twisted cellulose fiber materials, curled cellulose fiber materials, eucalyptus fiber materials, or combinations thereof.

5. The disposable absorbent article of claim 2, wherein the acquisition and acquisition/distribution layers of the first absorbent core component further comprise absorbent gelling materials.

6. The disposable absorbent article of claim 1, wherein the second absorbent core component comprises fibrous nonwoven materials, fibrous wet-laid web materials, open-celled polymeric foam materials, absorbent gelling materials, or combinations thereof.

7. The disposable absorbent article of claim 6, wherein the second absorbent core component comprises fibrous nonwoven materials and open-celled polymeric foam materials.

8. The disposable absorbent article of claim 6, wherein the second absorbent core component comprises fibrous nonwoven materials and absorbent gelling materials.

9. The disposable absorbent article of claim 1 wherein the second absorbent core component can be replaced by a replacement second core component having the same structure as the component which was removed.

10. The disposable absorbent article of claim 1, wherein the first absorbent core component further comprises a storage/redistribution layer.

11. The disposable absorbent article of claim 10, wherein the storage/redistribution layer of the first absorbent core component comprises fibrous nonwoven materials, fibrous wet-laid web materials, open-celled polymeric foam materials, absorbent gelling materials, or combinations thereof.

12. The disposable absorbent article of claim 11, wherein the storage/redistribution layer of the first absorbent core component comprises fibrous nonwoven materials and open-celled polymeric foam materials.

13. The disposable absorbent article of claim 11, wherein the storage/redistribution layer of the first absorbent core component comprises fibrous nonwoven materials and absorbent gelling materials.

14. The disposable absorbent article of claim 11, wherein the fibrous nonwoven materials of the storage/redistribution layer are polyester fiber materials, polyethylene fiber materials, polypropylene fiber materials, cotton fiber materials, cellulose fiber materials, chemically stiffened cellulose fiber materials, twisted cellulose fiber materials, curled cellulose fiber materials, eucalyptus fiber materials, or combinations thereof.

15. A disposable absorbent article, the article having a first waist region, a second waist region, and a crotch region positioned between the first waist region and the second waist region, the absorbent article further comprising:
    a backsheet joined to a fluid pervious topsheet, the backsheet comprising a web and being substantially liquid impervious except at a first discontinuity in the web and at a second discontinuity in the web; and
    an absorbent core disposed between the topsheet and the backsheet, the absorbent core comprising absorbent core components;
    wherein the absorbent core components comprise a multilayered first absorbent core component non-removably disposed in at least the crotch region and has an acquisition layer and an acquisition/distribution layer, and at least one removable second absorbent core component is removably disposed in the first waist region and is in fluid communication with the first absorbent core component, and wherein the backsheet filter comprises first access means for providing access to the removable second absorbent core component through the backsheet so that the removable second absorbent core component may be removed from the absorbent article through the backsheet without having to remove the absorbent article from a wearer, the first access means comprising the first discontinuity in the web, the first discontinuity being positioned in the first waist region, a first recloseable flap secured over the first discontinuity, and a first fastener for recloseably joining the first flap to the backsheet, and wherein the absorbent core further comprises at least one removable third absorbent core component removably disposed in the second waist region and in fluid communication with the first absorbent core component and the backsheet further comprises second access means for providing access to the removable third absorbent core component through the backsheet so that the removable third absorbent core component may be removed from the absorbent article through the backsheet without having to remove the absorbent article from the wearer, the second access means comprising the second discontinuity in the web, the second discontinuity being positioned in the second waist region, a second reclosable flap secured over the second discontinuity, and a second fastener for recloseably joining the second flap to the remainder of the backsheet.

16. The disposable absorbent article of claim 15, wherein the third absorbent core component comprises fibrous nonwoven materials, fibrous wet-laid web materials, open-celled polymeric foam materials, absorbent gelling materials, or combinations thereof.

17. The disposable absorbent article of claim 16, wherein the third absorbent core component comprises fibrous nonwoven materials and open-celled polymeric foam materials.

18. The disposable absorbent article of claim 16, wherein the third absorbent core component comprises fibrous nonwoven materials and absorbent gelling materials.

19. The disposable absorbent article of claim 1 wherein the third absorbent core component can be replaced by a replacement third core component having the same structure as the component which was removed.

\* \* \* \* \*

UNITED STATES PATENT AND TRADEMARK OFFICE
CERTIFICATE OF CORRECTION

PATENT NO. : 6,989,005 B1
APPLICATION NO. : 08/828005
DATED : January 24, 2006
INVENTOR(S) : Gary Dean LaVon et al.

It is certified that error appears in the above-identified patent and that said Letters Patent is hereby corrected as shown below:

<u>Column 1</u>

Line 33, delete "worm" and insert --worn--.

<u>Column 4</u>

Line 24, delete "referred" and insert --preferred--.

Line 40, delete "chasis" and insert --chassis--.

<u>Column 14</u>

Line 14, delete "for an" and insert --foam--.

Line 46, insert after the word ""initial"" insert a space.

Line 53, delete "referred" and insert --preferred--.

<u>Column 15</u>

Line 8, delete "signed" and insert --assigned--.

Line 31, delete "Homey" and insert --Horney--.

<u>Column 16</u>

Line 63, delete "we" and insert --are--.

<u>Column 18</u>

Line 9, delete "ring" and insert --curing--.

<u>Column 21</u>

Line 36, after "components" and insert --;--.

Line 37, delete "component" and insert --components--.

Line 39, delete "has" and insert --have--.

Line 43, after "and" delete --is--.

Line 58, delete "fist" and insert --first--.

<u>Column 22</u>

Line 64, delete "has" and insert --have--.

Line 67, after "component" delete --is--

UNITED STATES PATENT AND TRADEMARK OFFICE
CERTIFICATE OF CORRECTION

PATENT NO. : 6,989,005 B1
APPLICATION NO. : 08/828005
DATED : January 24, 2006
INVENTOR(S) : Gary Dean LaVon et al.

It is certified that error appears in the above-identified patent and that said Letters Patent is hereby corrected as shown below:

Column 23
Line 3, delete "filter" and insert --further--.

Line 13, insert after "the" insert --remainder of the--.

Line 19, delete "1" and insert --15--.

Signed and Sealed this

Fifth Day of September, 2006

JON W. DUDAS
*Director of the United States Patent and Trademark Office*